United States Patent
Schaller et al.

(10) Patent No.: US 10,646,349 B2
(45) Date of Patent: May 12, 2020

(54) EXPANDABLE BONE IMPLANT

(71) Applicant: DePuy Synthes Products, Inc., Raynham, MA (US)

(72) Inventors: Konrad Schaller, Grenchen (CH); Beat Lechmann, Grenchen (CH); Robert Frigg, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/899,014

(22) Filed: Feb. 19, 2018

(65) Prior Publication Data
US 2018/0168816 A1 Jun. 21, 2018

Related U.S. Application Data

(63) Continuation of application No. 15/164,762, filed on May 25, 2016, now Pat. No. 9,925,055, which is a
(Continued)

(51) Int. Cl.
*A61F 2/44* (2006.01)
*A61B 17/16* (2006.01)
(Continued)

(52) U.S. Cl.
CPC ............ *A61F 2/44* (2013.01); *A61B 17/149* (2016.11); *A61B 17/1642* (2013.01);
(Continued)

(58) Field of Classification Search
CPC ............ A61B 17/1662; A61B 17/1671; A61B 17/1637; A61B 17/1642
See application file for complete search history.

(56) References Cited

U.S. PATENT DOCUMENTS 5,059,193 A   10/1991   Kuslich
5,772,681 A    6/1998   Leoni
(Continued)

FOREIGN PATENT DOCUMENTS

JP   2007-505710 A    3/2007
JP   2008-539817 A   11/2008
(Continued)

OTHER PUBLICATIONS

U.S. Provisional Application filed May 8, 2009 by Konrad Schaller et. al., entitled "Fracture Augmentation in General and Transpedicular Osteotomy in Particular", U.S. Appl. No. 61/176,517.
(Continued)

*Primary Examiner* — Julianna N Harvey
*Assistant Examiner* — Christina Negrellirodriguez
(74) *Attorney, Agent, or Firm* — BakerHostetler

(57) ABSTRACT

An expandable implant includes an implant body defining an internal void, the implant body including a plurality of interconnected linkages. A first plurality of the linkages has an expansion characteristic that is different from a second plurality of the linkages. An expandable bladder is sized to be disposed in the internal void. The bladder defines a bore configured to receive an expansion material, such that the expansion material applies an expansion force against the bladder, which thereby applies the expansion force against the implant body so as to cause the first linkage to expand greater than the second linkage. The expandable implant can be placed in a fracture location so as to restore height to a fractured target bone.

19 Claims, 21 Drawing Sheets

Related U.S. Application Data continuation of application No. 14/947,365, filed on Nov. 20, 2015, now abandoned, which is a continuation of application No. 12/775,876, filed on May 7, 2010, now Pat. No. 9,216,023.

(60) Provisional application No. 61/176,517, filed on May 8, 2009.

(51) Int. Cl.
*A61B 17/70* (2006.01)
*A61B 17/14* (2006.01)
*A61B 17/88* (2006.01)
*A61F 2/28* (2006.01)
*A61F 2/46* (2006.01)

(52) U.S. Cl.
CPC ...... *A61B 17/1671* (2013.01); *A61B 17/7097* (2013.01); *A61B 17/8858* (2013.01); *A61F 2/28* (2013.01); *A61F 2/46* (2013.01); *A61F 2/4611* (2013.01); *A61B 17/1604* (2013.01); *A61F 2002/2835* (2013.01); *A61F 2002/4475* (2013.01); *A61F 2002/4625* (2013.01); *A61F 2002/4635* (2013.01)

(56) References Cited

U.S. PATENT DOCUMENTS

| | | | |
|---|---|---|---|
| 6,019,789 A | 2/2000 | Dinh et al. | |
| 6,127,597 A | 10/2000 | Beyar et al. | |
| 6,224,603 B1 | 5/2001 | Marino | |
| 6,293,967 B1 | 9/2001 | Shanley | |
| 6,582,467 B1 | 6/2003 | Teitelbaum et al. | |
| 6,632,235 B2 | 10/2003 | Weikel et al. | |
| 7,001,431 B2 | 2/2006 | Bao et al. | |
| 7,141,061 B2 | 11/2006 | Williams et al. | |
| 7,465,318 B2 | 12/2008 | Sennett et al. | |
| 7,601,172 B2 | 10/2009 | Segal et al. | |
| 7,666,205 B2 | 2/2010 | Weikel et al. | |
| 7,678,142 B2 | 3/2010 | Vardi et al. | |
| 7,842,040 B2 | 11/2010 | Rabiner et al. | |
| 7,879,041 B2 | 2/2011 | Rabiner et al. | |
| 7,988,735 B2 | 8/2011 | Yurek et al. | |
| 8,021,426 B2 | 9/2011 | Segal et al. | |
| 8,287,538 B2 | 10/2012 | Brenzel et al. | |
| 9,216,023 B2 | 12/2015 | Schaller et al. | |
| 9,925,055 B2 * | 3/2018 | Schaller | A61B 17/1642 |
| 2004/0100706 A1 | 5/2004 | Van et al. | |
| 2004/0167625 A1 | 8/2004 | Beyar et al. | |
| 2004/0186551 A1 | 9/2004 | Kao et al. | |
| 2005/0070913 A1 | 3/2005 | Milbocker et al. | |
| 2005/0209629 A1 | 9/2005 | Kerr et al. | |
| 2006/0004437 A1 | 1/2006 | Jayaraman | |
| 2006/0025861 A1 | 2/2006 | McKay | |
| 2006/0100706 A1 | 5/2006 | Shadduck et al. | |
| 2006/0184188 A1 | 8/2006 | Li et al. | |
| 2006/0271061 A1 | 11/2006 | Beyar et al. | |
| 2006/0287726 A1 | 12/2006 | Segal et al. | |
| 2006/0287727 A1 | 12/2006 | Segal et al. | |
| 2007/0016191 A1 | 1/2007 | Culbert et al. | |
| 2007/0043440 A1 | 2/2007 | William et al. | |
| 2007/0088436 A1 | 4/2007 | Parsons et al. | |
| 2007/0093899 A1 | 4/2007 | Dutoit et al. | |
| 2007/0161991 A1 | 7/2007 | Altarac et al. | |
| 2007/0179610 A1 | 8/2007 | Biedermann et al. | |
| 2007/0255287 A1 | 11/2007 | Rabiner | |
| 2007/0260252 A1 | 11/2007 | Schmitz et al. | |
| 2008/0071356 A1 | 3/2008 | Greenhalgh et al. | |
| 2008/0125784 A1 | 5/2008 | Rabiner et al. | |
| 2008/0208255 A1 | 8/2008 | Siegal | |
| 2008/0208320 A1 | 8/2008 | Tan-Malecki et al. | |
| 2008/0249481 A1 | 10/2008 | Crainich et al. | |
| 2008/0294205 A1 | 11/2008 | Greenhalgh et al. | |
| 2009/0024204 A1 | 1/2009 | Greenhalgh et al. | |
| 2009/0105809 A1 | 4/2009 | Lee et al. | |
| 2009/0131992 A1 | 5/2009 | Greenhalgh et al. | |
| 2009/0177204 A1 | 7/2009 | Colleran et al. | |
| 2009/0187192 A1 | 7/2009 | Rabiner et al. | |
| 2009/0204216 A1 | 8/2009 | Biedermann et al. | |
| 2009/0254186 A1 * | 10/2009 | Tornier | A61F 2/442 623/17.16 |
| 2010/0121333 A1 | 5/2010 | Crainich et al. | |
| 2010/0286782 A1 | 11/2010 | Schaller et al. | |
| 2011/0028978 A1 | 2/2011 | Li et al. | |
| 2011/0046737 A1 | 2/2011 | Teisen | |
| 2011/0112643 A1 | 5/2011 | Schwab | |
| 2011/0264147 A1 | 10/2011 | Culbert | |
| 2016/0074086 A1 | 3/2016 | Schaller et al. | |

FOREIGN PATENT DOCUMENTS

| | | |
|---|---|---|
| JP | 4667716 B2 | 4/2011 |
| JP | 5112295 B2 | 1/2013 |
| JP | 5213138 B2 | 6/2013 |
| JP | 5542273 B2 | 7/2014 |
| WO | 02/71975 A2 | 9/2002 |
| WO | 2004/110300 A2 | 12/2004 |
| WO | 2005/027734 A2 | 3/2005 |
| WO | 2006/116761 A2 | 11/2006 |
| WO | 2007/076376 A2 | 7/2007 |
| WO | 2007/078692 A2 | 7/2007 |
| WO | 2007/131002 A2 | 11/2007 |
| WO | 2008/070867 A2 | 6/2008 |
| WO | 2010/129846 A1 | 11/2010 |

OTHER PUBLICATIONS

International Patent Application No. PCT/US2010/033995: International Search Report dated Jul. 26, 2010, 8 pages.
Fracture Augmentation in General and Transpedicular Osteotomy in Particular, U.S. Appl. No. 61/176,517.

* cited by examiner

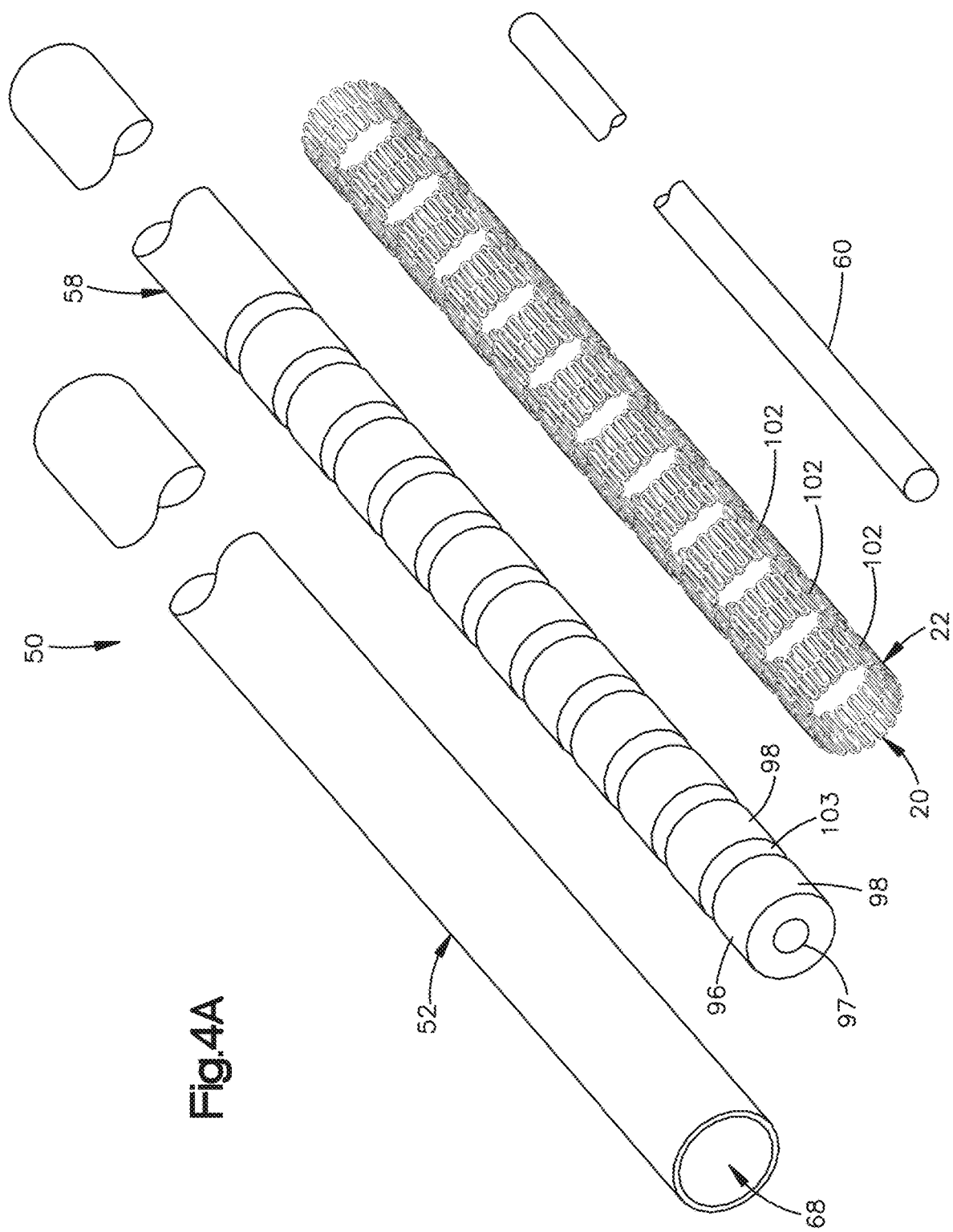

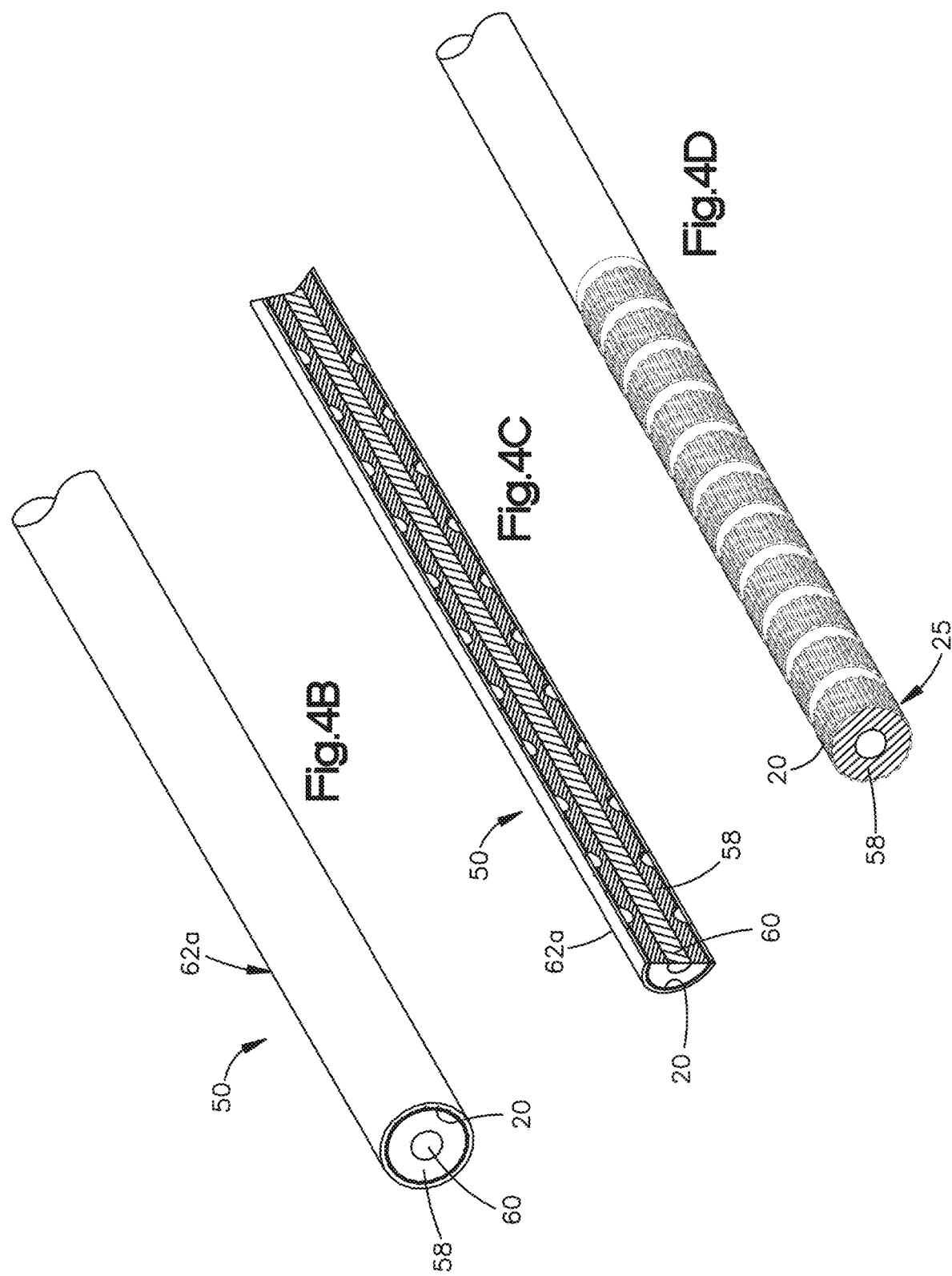

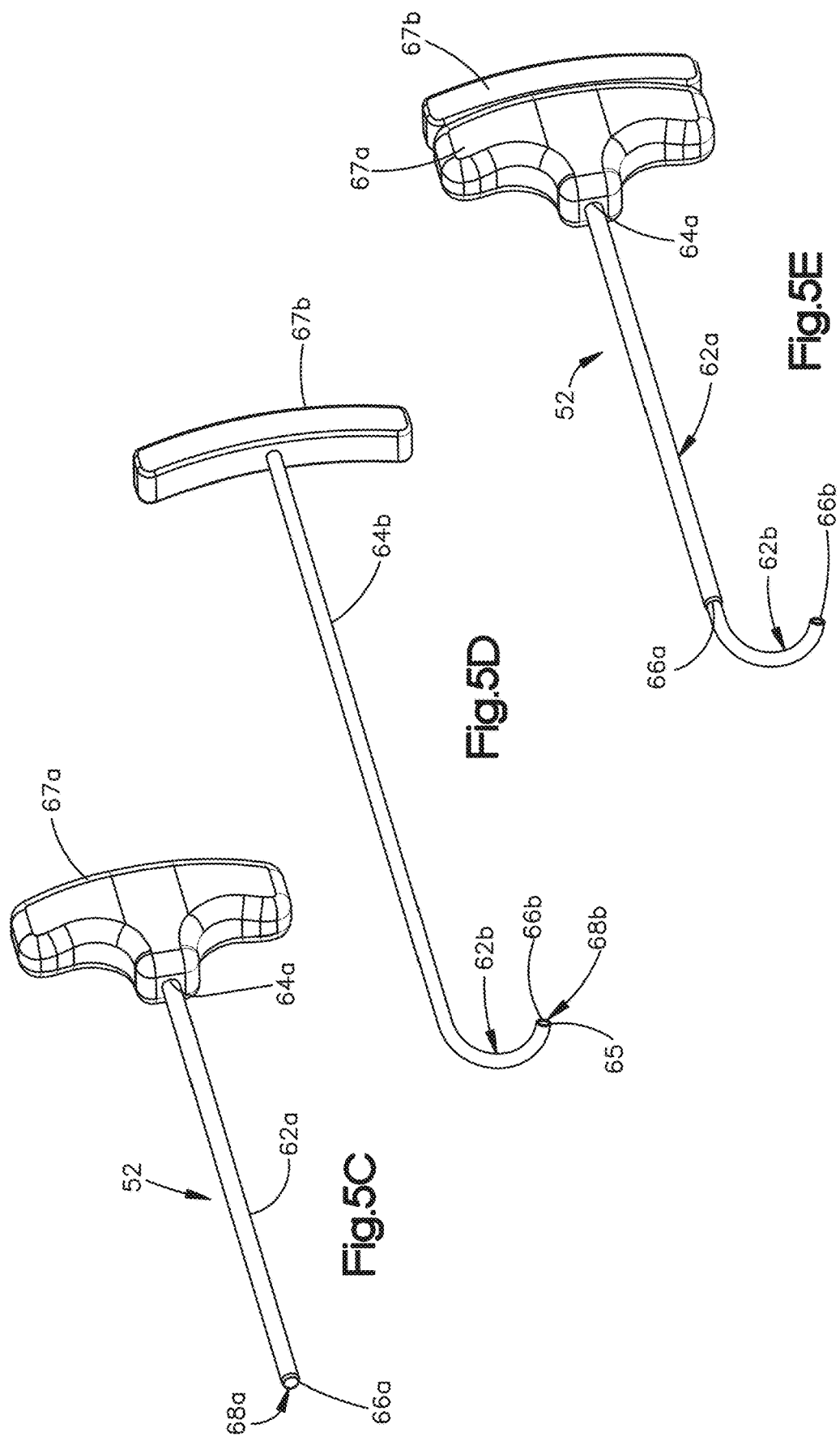

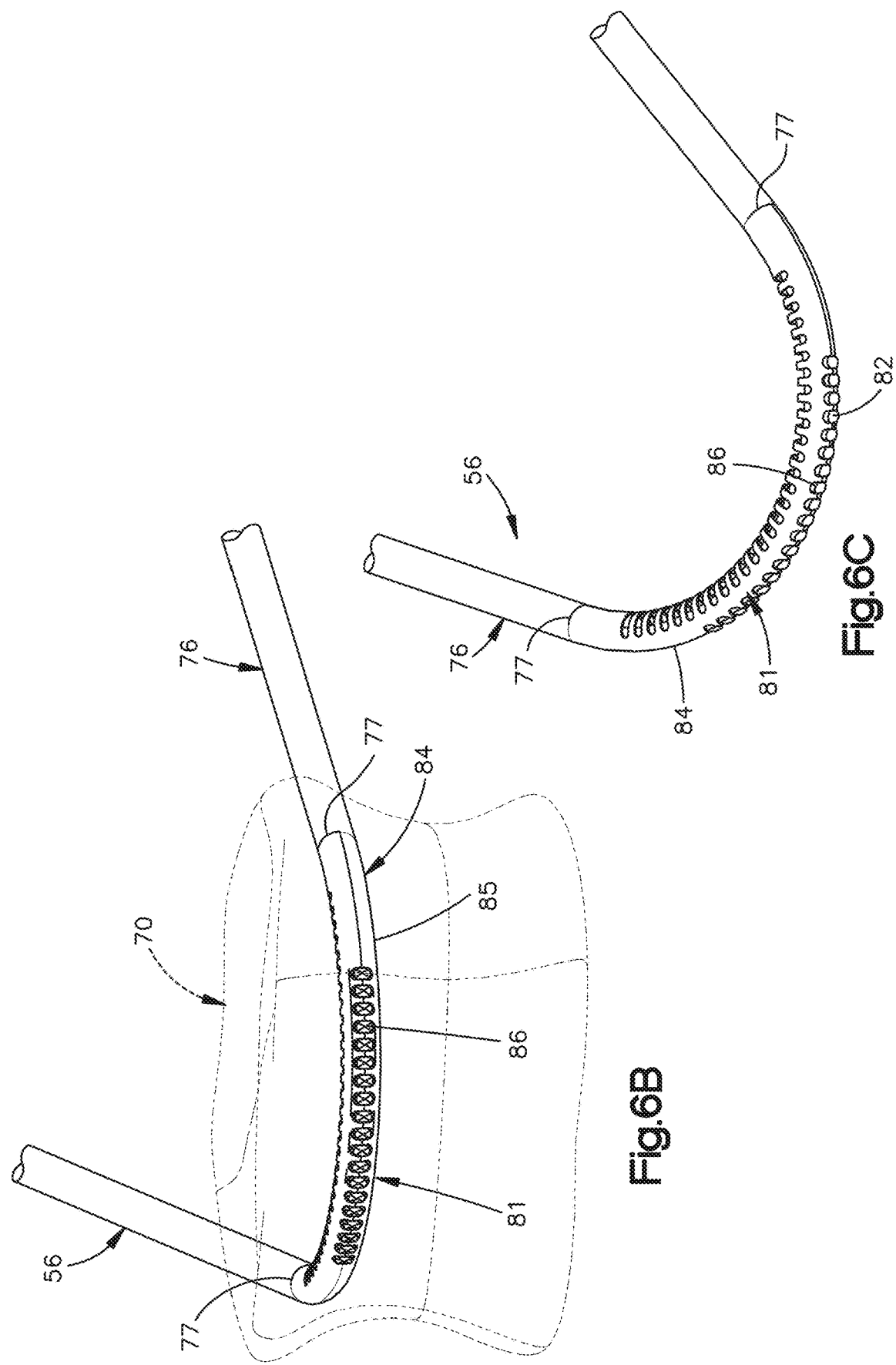

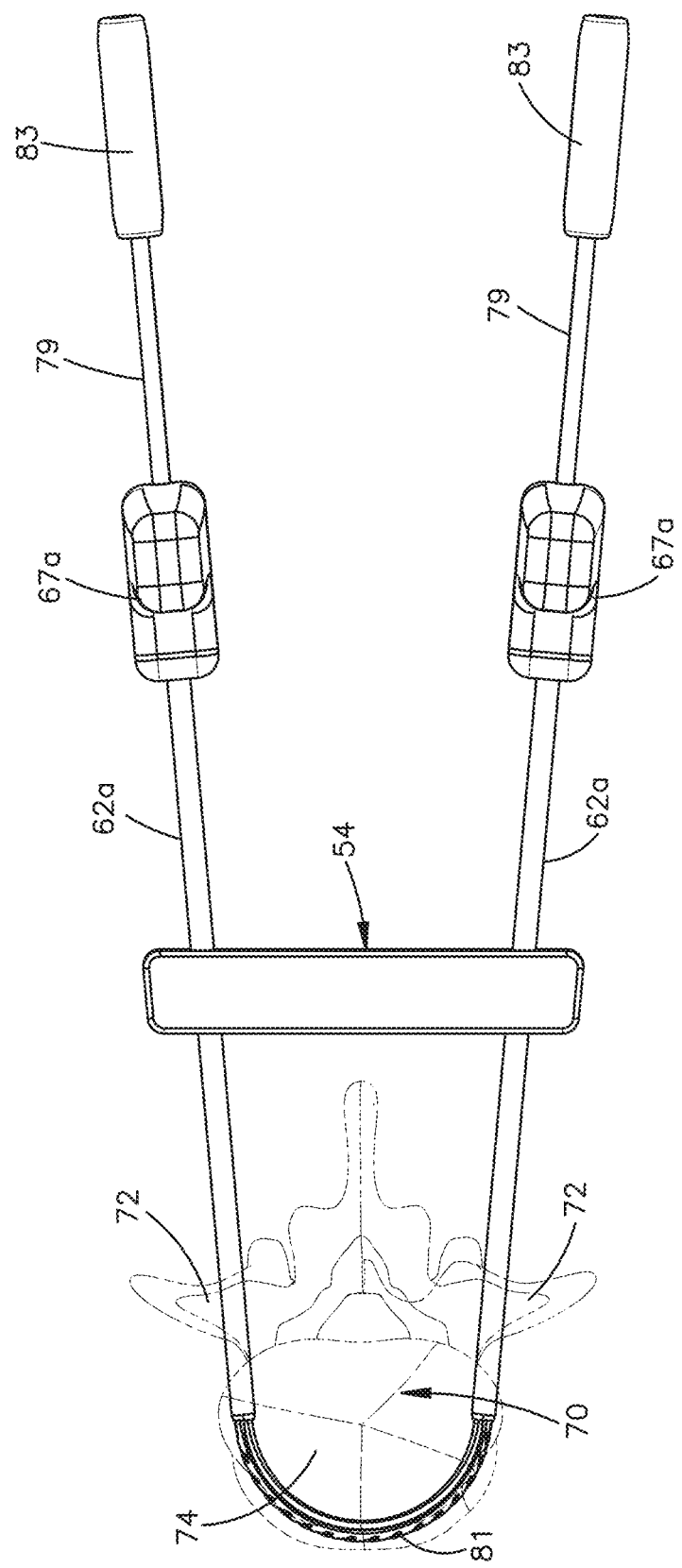

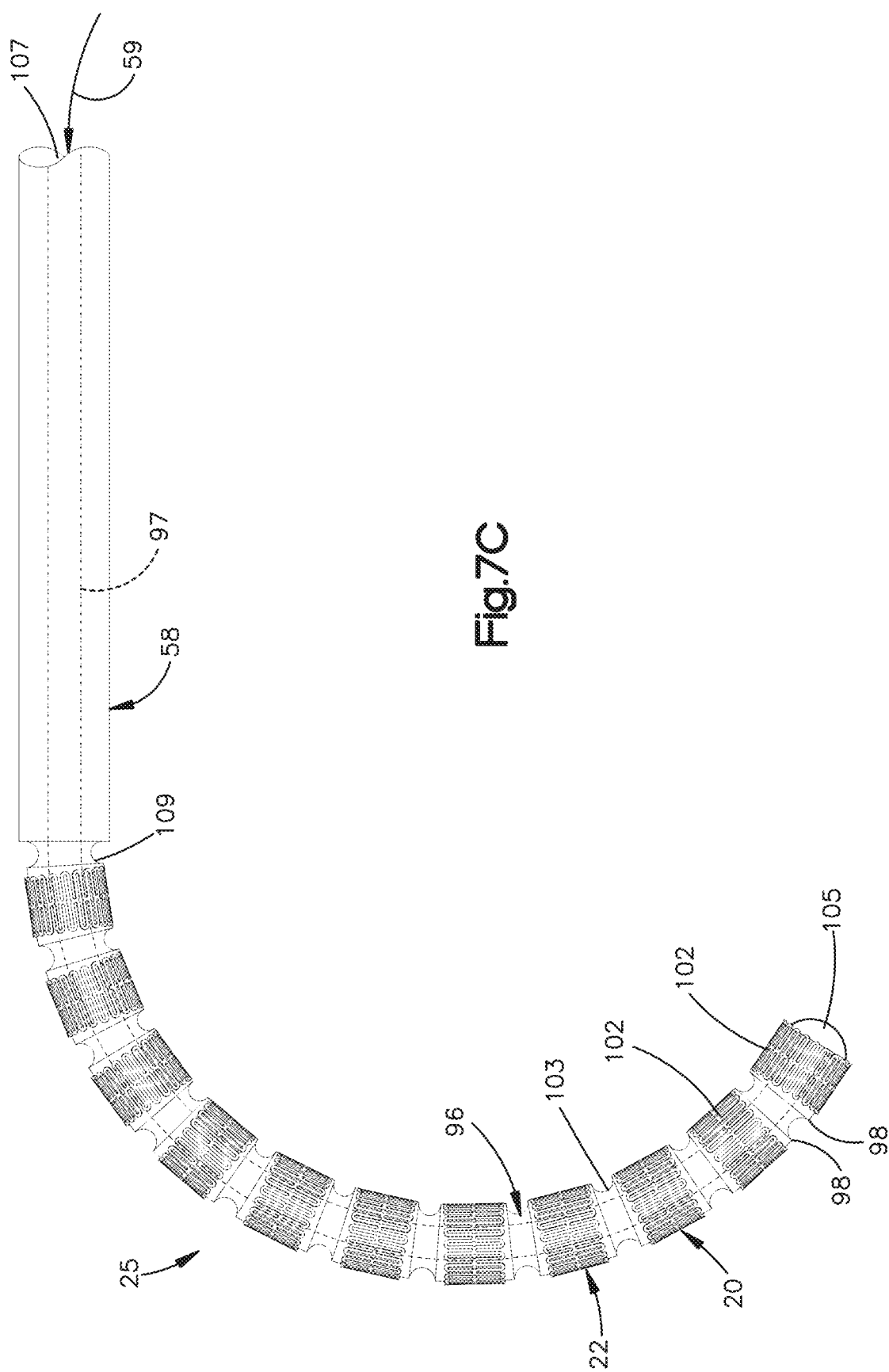

EXPANDABLE BONE IMPLANT

CROSS-REFERENCE TO RELATED APPLICATIONS

This application is a continuation of U.S. patent application Ser. No. 15/164,762 filed May 25, 2016, which is a continuation of U.S. patent application Ser. No. 14/947,365, filed Nov. 20, 2015, which is a continuation of U.S. patent application Ser. No. 12/775,876, filed May 7, 2010, now U.S. Pat. No. 9,216,023, issued Dec. 22, 2015, which claims priority to and the benefit of U.S. Provisional Patent Application Ser. No. 61/176,517, filed on May 8, 2009. The disclosures of each application listed in this paragraph is hereby incorporated by reference as if set forth in its entirety herein.

BACKGROUND

Vertebral compression fractures ("VCF") represent a common spinal injury and may result in prolonged disability. Generally speaking, VCF involves collapsing of one or more vertebral bodies in the spine. VCF usually occurs in the lower vertebrae of the thoracic spine or the upper vertebrae of the lumbar spine. VCF generally involves fracture of the anterior portion of the affected vertebral body. VCF may result in deformation of the normal alignment or curvature, e.g., lordosis, of the vertebral bodies in the affected area of the spine. VCF and/or related spinal deformities may result, for example, from metastatic diseases of the spine, from trauma or may be associated with osteoporosis. Until recently, doctors were limited in how they could treat VCF and related deformities.

Recently, minimally invasive surgical procedures for treating VCF have been developed. These procedures generally involve the use of a cannula or other access tool inserted into the posterior of the targeted vertebral body, usually through the pedicles.

In one such procedure, a cannula or bone needle is passed through the soft tissue of the patient's back. Once properly positioned, a small amount of polymethylmethacrylate (PMMA) or other orthopedic bone cement is pushed through the needle into the targeted vertebral body. This technique may be effective in the reduction or elimination of fracture pain, prevention of further collapse, and a return to mobility in patients. However, this technique typically does not reposition the fractured bone into its original size and/or shape and, therefore, may not address the problem of spinal deformity due to the fracture.

Other treatments for VCF generally involve two phases: (1) reposition or restoration of the original height of the vertebral body and consequent lordotic correction of the spinal curvature; and (2) augmentation or addition of material to support or strengthen the fractured or collapsed vertebral body.

One such treatment involves inserting, through a cannula, a catheter having an expandable member into an interior volume of a fractured vertebral body, wherein the interior volume has a relatively soft cancellous bone surrounded by fractured cortical bone therein. The expandable member is expanded within the interior volume in an attempt to restore the vertebral body towards its original height. The expandable member is removed from the interior volume, leaving a void within the vertebral body. PMMA or other bone filler material is injected through the cannula into the void to stabilize the vertebral body. The cannula is then removed and the cement cures to augment, fill or fix the vertebral body.

Another approach for treating VCF involves inserting an expandable mesh graft bladder or containment device into the targeted vertebral body. The graft bladder remains inside the vertebral body after it is inflated with PMMA or an allograft product, which limits intra-operative loss of height of the repositioned endplates.

It is desirable in the art to provide a safe and effective apparatus and method for aiding and/or augmenting fractured or otherwise damaged vertebral bodies and other bones, preferably an apparatus that reestablishes the vertebral body's height and which may be inserted via a minimally invasive surgical technique.

SUMMARY

In accordance with one embodiment, an expandable implant is configured to restore height to a fractured target bone. The expandable implant includes a body having a plurality of linkages connected so as to define at least one annular row. The linkages define first and second opposed side portions connected by corresponding first and second end portions. The first and second side portions define a distance therebetween when the body is in an insertion configuration. When the linkages are subjected to an expansion force, the body expands to an expanded configuration, such that the distance between the first and second side portions increases from a first distance to a second distance that is greater than the first distance. At least a first linkage of the plurality of linkages is sized different than at least a second linkage of the plurality of linkages such that the first linkage expands greater than the second linkage.

DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings:

FIG. 4A is an exploded perspective view of an implant system constructed in accordance with one embodiment;

FIG. 4B is a partial perspective view of the implant system illustrated in FIG. 4A;

FIG. 4C is a sectional view of the implant system illustrated in FIG. 4B;

FIG. 4D is a partial perspective view of an expandable implant assembly included in the implant system illustrated in FIG. 4C;

FIG. 5C is a perspective view of one of the cannulas illustrated in FIG. 5A;

FIG. 5D is a perspective view of a portion of one of the opening devices illustrated in FIG. 5A;

FIG. 5E is a perspective view of the opening assembly including the opening device illustrated in FIG. 5D inserted into the cannula illustrated in FIG. 5C;

FIG. 6B is an enlarged perspective view of the cutting device illustrated in FIG. 6A shown in an insertion configuration having cutting teeth retracted;

FIG. 6C is a perspective view of the cutting device illustrated in FIG. 6B, shown in a cutting configuration having the cutting teeth extended;

FIG. 6D is a perspective view similar to FIG. 6A, but showing the opening device removed;

FIG. 7C is a side elevation view of the implant assembly illustrated in FIG. 7B, receiving a filler material;

DETAILED DESCRIPTION

Figure 1A:
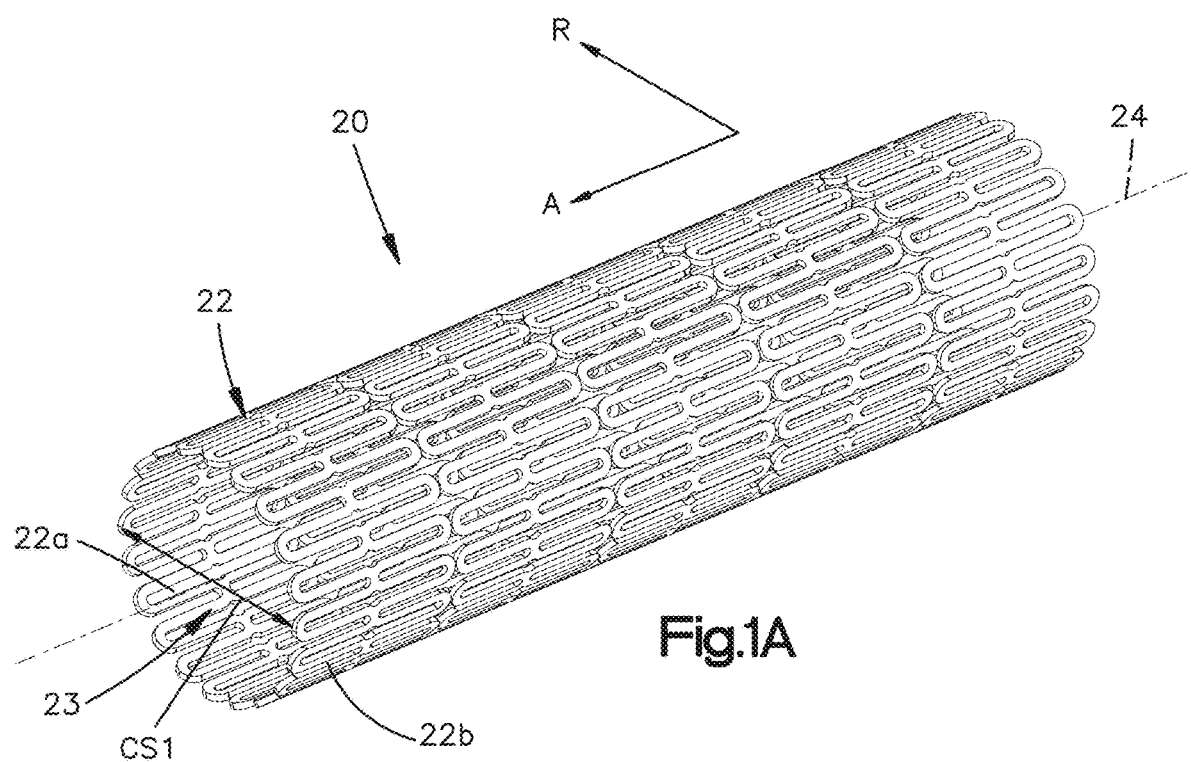
FIG. 1A is a perspective view of an expandable implant shown in an insertion configuration.
Figure 1B:
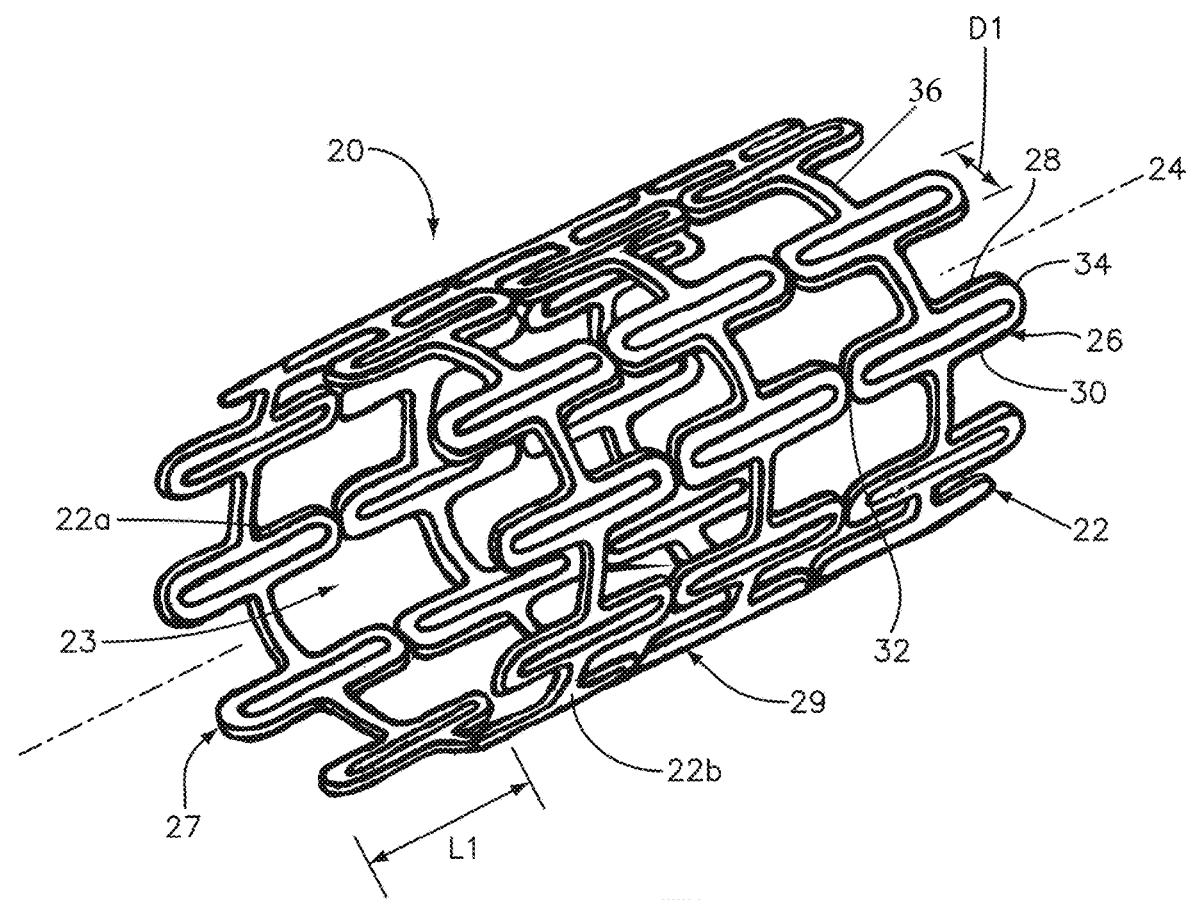
FIG. 1B is an enlarged perspective view of a portion of the expandable implant illustrated in FIG. 1.
Figure 1C:
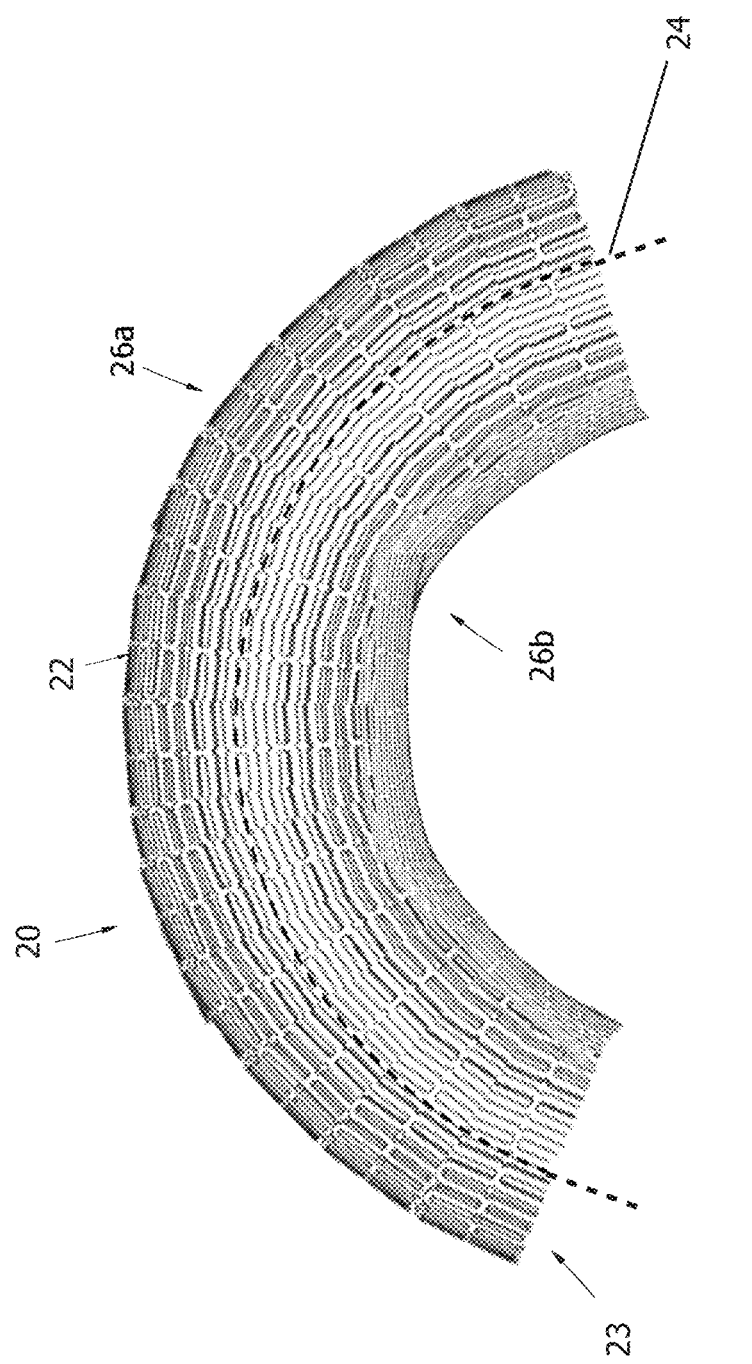
FIG. 1C is an enlarged perspective view of a portion of the expandable implant illustrated in FIG. 1.

Referring initially to FIGS. 1A-B, an expandable augmentation implant 20 is configured to be inserted into a target bone, such as a vertebral body of a vertebra. In accordance with one aspect of the present disclosure, the expandable insert 20 is configured to be inserted into the vertebral body of a vertebra that has been subjected to trauma, such as a vertebral compression fracture ("VCF"). As will be appreciated from the description below, the implant 20 is configured to be implanted via a minimally invasive surgical technique, such as, for example, through one or more cannulas, preformed holes or percutaneously. Once implanted, the expandable implant 20 is configured to reposition and stabilize the target bone to re-establish structural integrity and reduce or eliminate painful micro-movements.

Thus, the implant 20 has a first insertion configuration having a corresponding first insertion size that is configured to allow the implant 20 to be inserted into an interior volume of the target bone. Once inserted into the target bone, the expandable implant can be expanded from the insertion configuration to a second expanded configuration having a corresponding second expanded size that is greater than the insertion size. When in the expanded configuration, the implant 20 can generally create a cavity within the interior volume of the target bone, restore the height of and stabilize the target bone, and occupy a portion of, or augment, the interior volume of the targeted bone.

The implant 20 is illustrated as including a substantially annular implant body 22 disposed about a central axis 24 that extends in an axial direction A. The implant 20 can be made from a polymeric material with directed fibres, and can be coated if desired with one or more antibiotic agents in order to inhibit infections. In accordance with one embodiment, the implant 20 is made from a Phynox material. The implant 20 can further be coated with an osteoconductive layer such as sprayed Hydroxyapatite or other Ca and P compositions. The implant 20 can be manufactured by selective laser melting or sintering process in order to change the bar geometry homogeneously.

The implant body 22 includes an inner surface 22a that defines an internal void 23, and an opposed outer surface 22b. The implant body 22 includes a plurality of connected linkages 26. Each linkage 26 includes a first and second opposed flexible side portions 28 and 30, respectively, and first and second opposed flexible end portions 32 and 34, respectively, connected between the side portions 28 and 30. The end portions 32 and 34 are curved and define a radius of curvature in accordance with the illustrated embodiment, though it should be appreciated that the end portions can define any suitable shape as desired. Likewise, the side portions 28 and 30 are substantially straight and parallel along the axial direction when the implant 20 is in the insertion configuration, though it should be appreciated that the side portions 28 and 30 can define any suitable shape and spatial relationship as desired.

In accordance with the illustrated embodiment, the linkages 26 are arranged in at least one, such as a plurality of, columns 27, and at least one, such as a plurality of, rows 29. The columns 27 extend along a column direction that is coincident with the axial direction A in the illustrated embodiment. The rows 29 extend along a row direction that is circumferential so as to define an annulus in the illustrated embodiment. The ends of the linkages 26 are integrally or directly connected to each other along the column direction as illustrated, though it should be appreciated that the linkages 26 could alternatively be connected to each other indirectly via a connection member. The sides of the linkages 26 are indirectly connected to each other via corresponding circumferential arms 36, though it should be appreciated that the sides of the linkages 26 could alternatively be directly connected to each other. It can thus be said that the linkages 26 are connected to each other, either indirectly or indirectly, along the column and row directions so as to define respective columns 27 and rows 29.

In accordance with one embodiment, the side portions 28 and 30 extend axially, that is they extend along a direction having an axial component. Otherwise stated, the side portions 28 and 30 extend along a direction that is angularly offset with respect to a radial direction R that extends along a direction perpendicular with respect to the central axis 24. Accordingly, as will be appreciated from the description below, the side portions 32 and 34 are configured to expand when a radially outward force is applied to the implant body 22. For instance, as will be described in more detail below, an expansion device 58, such as an expandable bladder (see FIGS. 4A-D), can be placed inside the implant body 22, and an expansion material can be injected into the bladder to expand the bladder and, consequently, to expand the implant body 22.

In accordance with the embodiment illustrated in FIGS. 1A-B, when the implant 20 is in the insertion configuration, each given linkage defines a length L1 that extends between the opposed end portions 32 and 34. Furthermore, when the implant 20 is in the insertion configuration, the side portions 28 and 30 extend substantially parallel to each other and are separated from each other by a first or insertion distance D1, which extends circumferentially in accordance with the illustrated embodiment. Otherwise stated, the side portions 28 and 30 are separated by the first distance D1 at a select location along the length of the side portions 28 and 30. Thus, the circumference of the implant body 22 is at least partially defined by the first distance D1. When the implant 20 is in the insertion configuration, the implant body 22 defines a first cross-sectional distance CS1, which can be a diameter, for instance when the implant defines a cylindrical surface as illustrated. The first cross-sectional distance CS1, and thus the first distance D1, provides the implant 20 with the first insertion size that is configured to allow the implant 20 to be inserted into an interior volume of the target bone.

Figure 2A:
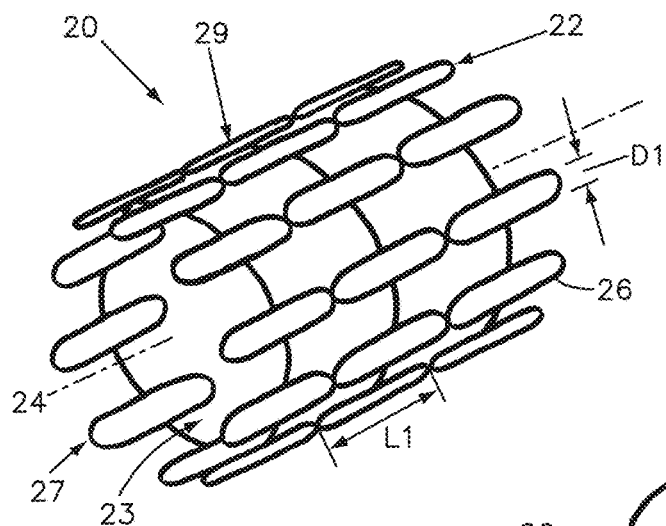
FIG. 2A is a schematic perspective view of the portion of the expandable implant illustrated in FIG. 1B.
Figure 2B:
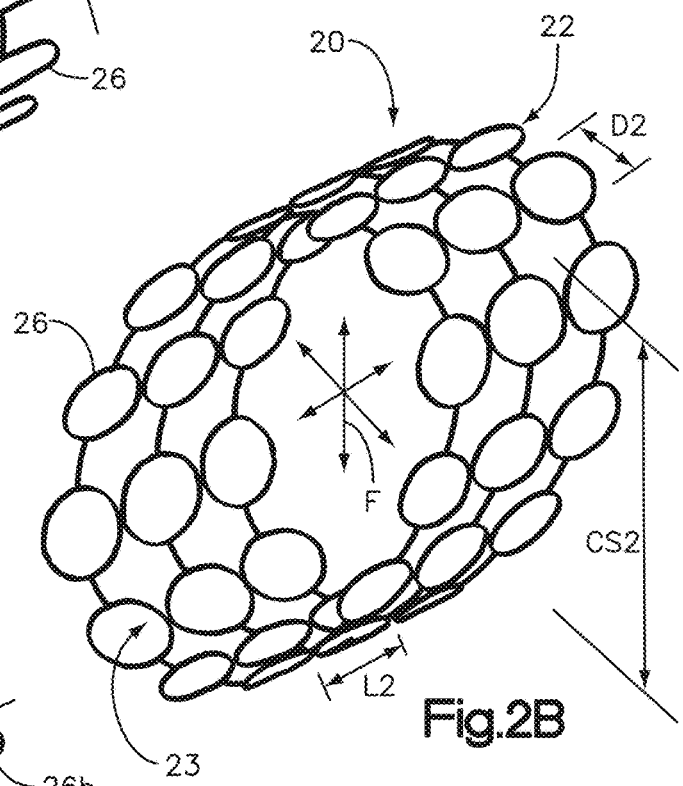
FIG. 2B is a schematic perspective view similar to FIG. 2A, but showing the implant in an expanded configuration.

The expandable implant 20 is configured to expand from the insertion configuration illustrated in FIGS. 1A-B to the expanded configuration illustrated in FIGS. 2A-B. As illustrated in FIG. 2A, each linkage 26 is substantially identically constructed, and thus defines substantially the same initial length L1 and distance D1 as the other linkages 26. The implant 20 can be expanded from its insertion configuration to its expanded configuration by inserting a sufficient volume of thermosetting bone filler material into the internal void 23 of the implant 20, such that the material fills the void 23 and applies a radially outward expansion force F against the linkages 26. The bone filler material may be, for instance, in the form of bone chips, allograft bone, or a biocompatible bone cement. One example of a suitable biocompatible bone cement is a self-hardening (e.g. self-curing) polymethylmethacrylate (PMMA), though it should be appreciated that the bone filler material can be selected from any suitable bone filling material as desired.

Referring to FIG. 2B, when the radially outward expansion force F is applied to the inner surface of the linkage body 22, and in particular to the linkages 26, the linkages 26 expand. For instance, the initial distance extending between the side portion 28 and 30 of at least one up to all of the linkages 26 increases from the first insertion distance D1 to a second expanded distance D2 that is greater than the first insertion distance D1. Simultaneously, the length of at least one up to all of the linkages 26 is reduced from the first length L1 to a second expanded length L2 that is less than the first insertion length L2. Assuming that the expansion force F is distributed uniformly about the implant body 22, the identically constructed linkages 26 will expand substantially uniformly, and the implant body 22 will expand to a second expanded cross-sectional distance or diameter CS2 that is greater than the first insertion cross-sectional distance or diameter CS1.

Figure 3A:
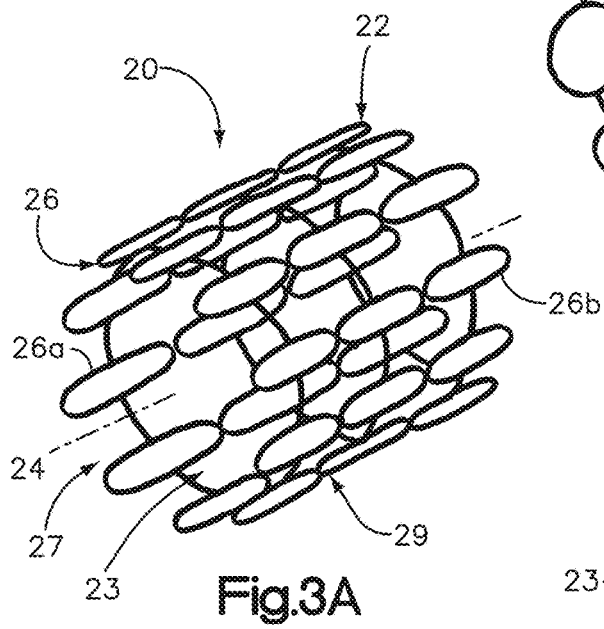
FIG. 3A is a schematic perspective view similar to FIG. 2A, but showing the implant constructed in accordance with an alternative embodiment.

While the linkages 26 can all be substantially identically constructed as described above with respect to FIGS. 2A-B, it is appreciated that at least one, such as a first plurality, of the linkages 26 can be constructed differently than at least one, such as a second plurality, of the linkages 26. For instance, referring now to FIG. 3A the expandable implant 20 is illustrated in its insertion configuration in accordance with an alternative embodiment. As illustrated, the implant 20 includes a first plurality of linkages 26a (see also FIG. 3C) and a second plurality of linkages 26b (see also FIG. 3D). The linkages 26a can be circumferentially spaced from the linkages 26b, such that they are circumferentially opposed to each other. Otherwise stated, a first select number of columns 27, and in particular adjacent columns 27 can include linkages 26a, while a second select number of columns 27, and in particular adjacent columns 27, can include linkages 26b. Alternatively or additionally, the linkages 26a can be axially spaced from the linkages 26b, such that a first select number of rows 29, and in particular adjacent rows 29, can include linkages 26a, while a second select number of rows 29, and in particular adjacent rows 29, can include linkages 26b.

Figure 3B:
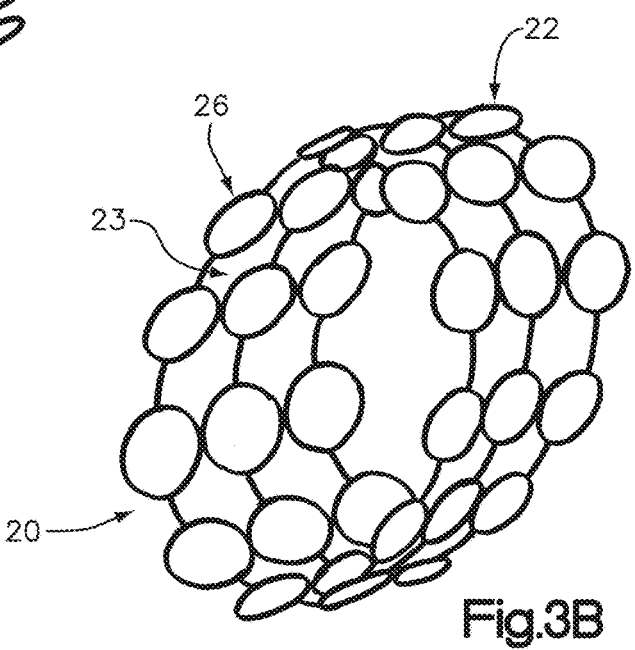
FIG. 3B is a schematic perspective view similar to FIG. 3A, but showing the implant in an expanded configuration.
Figure 3C:
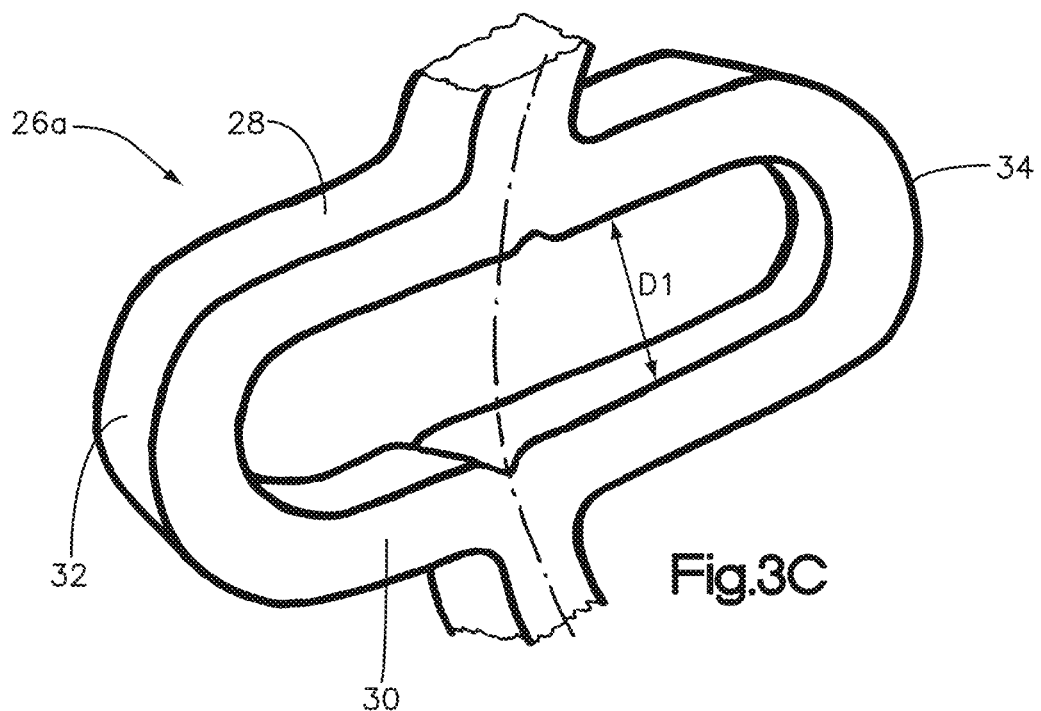
FIG. 3C is a perspective view of a first linkage of the implant illustrated in FIG. 3A.
Figure 3D:
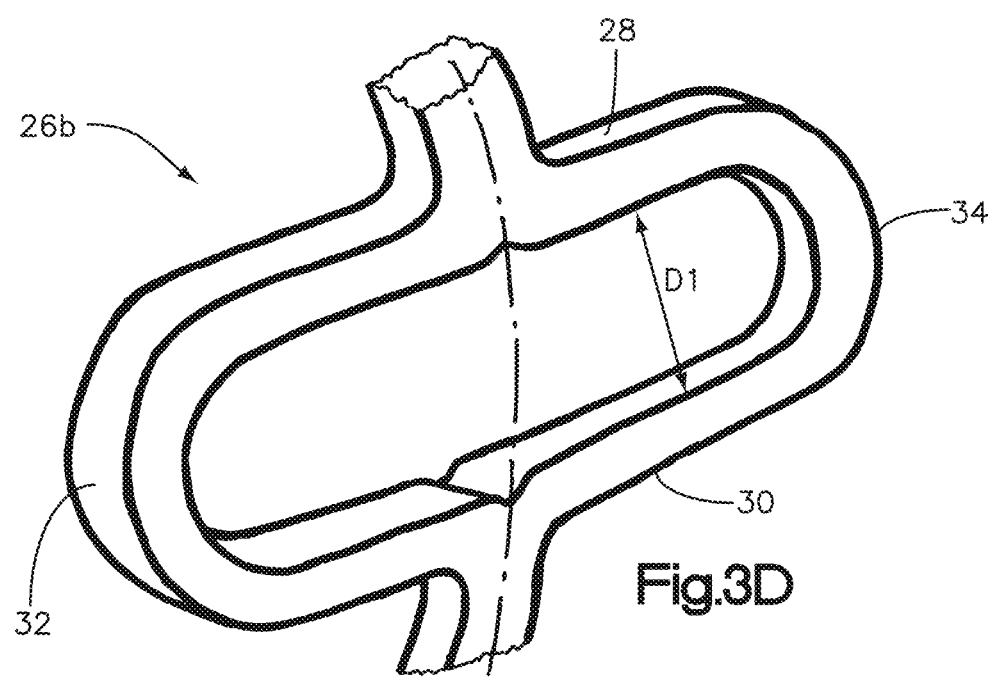
FIG. 3D is a perspective view of a second linkage of the implant illustrated in FIG. 3A.

In accordance with the illustrated embodiment, the first insertion length L1 of the first plurality of linkages 26a is greater than the first insertion length L1 of the second plurality of linkages 26b when the implant 20 is in the insertion configuration, such that the distance D1 of the first plurality of linkages 26a is substantially equal to the distance D1 of the second plurality of linkages 26b (thought the distances D1 could be different between the linkages 26a and the linkages 26b as desired). It should thus be appreciated that the distance D1 of the first plurality of linkages 26a is configured to expand greater than the distance D1 of the second plurality of linkages 26b. In accordance with one embodiment, the first plurality of linkages 26a expands at a greater rate than the second plurality of linkages 26b when subjected to substantially the same expansion force as the second plurality of linkages 26b. Thus, the implant 20 can be configured to produce a symmetric shape under a uniform expansion force as illustrated in FIG. 2B, or the implant 20 can be configured to produce an asymmetric shape under a uniform expansion force as illustrated in FIG. 3B.

In accordance with one embodiment, the implant 20 is inserted into the target bold in its insertion configuration, whereby the linkages 26 can be referred to as in a compressed or folded configuration, such that the implant 20 can be passed through a cannula, through the openings formed in the pedicles and into an interior cavity of the targeted vertebral body as described in more detail below. The implant 20 follows a curved guide path of a bent guide wire in accordance with one embodiment, and as a result the implant 20 can be flexible so as to follow the curved guide path. However, the in situ bending of the implant 20 while traveling along the guide path can lead to plastic deformation in order the provide the implant with appropriate structural stability. Expansion of the implant 20 by, for example, injection of a bone filler material causes the structure of the implant 20 to exceed the elastic phase of the material and hence results in plastic deformation of the implant 20. When the target bone is a vertebral body, the plastic deformation of the implant allows the implant 20 to provide augmentation in the anterior aspect of the vertebral body.

When the implant 20 includes the first plurality of linkages 26a and the second plurality of linkages 26b, Hooke's Law demonstrates that the implant body 22 can assume an asymmetrical or bent shape when the implant body 22 is expanded elastically. It should be appreciated, however, that expansion of the linkages 26a and 26b occurs beyond the elastic deformation limit, such that the implant body 22 can also undergo some amount of plastic deformation. Due to the later injected bone filler material, the implant is frozen at the achieved expansion.

Example Embodiment—Application of the Hooke's Law

Definitions

ε Strain
σ Tensile Strength
A Cross-sectional area of bar
$A_i$ 0.4 mm2;
$A_o$ 0.2 mm2
l Length of bar
$l_i$ 8 mm
$l_o$ 10 mm
E Modulus of Elasticity Phynox: 203-400 Mpa
Elongation: $\Delta l = \varepsilon \cdot l$
Whereas strain is: $\varepsilon = \sigma / E$
And: $\Delta l = \sigma \cdot l / E$ Assumption, where "i" indicates the region of the implant body 22 having the second plurality of linkages 26b (which can be located at a circumferentially inner end of the implant body 22), while "o" indicates the region of the implant body 22 having the first plurality of linkages 26a (which can be located at a circumferentially outer end of the implant body 22), and the expansion is under a substantially uniform expansion force (or tensile force). The resulting tensile strength of the second plurality of linkages 26b and the first plurality of linkages 26a, respectively, is as follows:

$$\sigma_i = F/A_i = 120 N/0.2 \text{ mm2} = 600 \text{ [N/mm2]}$$

$$\sigma_o = F/A_o = 120 N/0.4 \text{ mm2} = 300 \text{ [N/mm2]}$$

The resulting elongation of the second plurality of linkages 26b and the first plurality of linkages 26a, respectively, is as follows:

$$\Delta l_i = \sigma_i \cdot l_i / E = 300 \text{ MPa} \cdot 8 \text{ mm} / 203,400 \text{ MPa} = 0.011 \text{ mm}$$

$$\Delta l_o = \sigma_o \cdot l_o / E = 600 \text{ MPa} \cdot 10 \text{ mm} / 203,400 \text{ MPa} = 0.030 \text{ mm}$$

Based on this analysis, the implant 20 expands at the region of linkages 26a significantly more than at the region of linkages 26b (approximately 3 fold in above-identified example). Consequently, the implant 20 becomes bent during expansion since the second plurality of linkages 26b has a smaller elongation compared to the first plurality of linkages 26a. It should be appreciated that the numbers of the above example are merely assumptions used to demonstrate the bending effect based on different linkage sizes of the expansion implant 20, and do not represent actual test data.

Referring now to FIGS. 4A-D, it is envisioned that an implant system 50 can include the implant 20 along with system apparatus that facilitate the insertion and expansion of the implant 20 within a target bone. For instance, the system 50 can include an opening assembly 52 including a cannulated body 62a, an opening device 62b (see FIG. 5A) that is received inside the cannulated body 62a, an aiming device 54 (see FIG. 5A) that supports the opening assembly 52, a cutting device 56 (see FIGS. 6A-F) that is configured to perform an osteotomy, and an expandable implant assembly 25 that includes the implant 20 that is configured to provide a bone augmentation and an expansion device 58 configured to iterate the implant 20 from the insertion configuration to the expanded configuration. The system 50 can further include a bone filler material device that is configured to be inserted into the expansion device 58 under pressure so as to expand the expansion device 58 against the implant 20. The system 50 can also include a guide 60 that provides a guide path for the implant 20 into the target bone. It should be appreciated that the system 50 can also include a osteotomy cutting device 56, which can be provided by the guide 60, or can alternatively be provided separate from the guide 60 as illustrated in FIGS. 6A-F.

Referring also to FIGS. 5A-D, the opening assembly 52 includes an elongate cannulated body 62a that defines a proximal end 64a and an opposed distal end 66a, and a cannula 68a that extends through the cannulated body 62a from the proximal end 64a to the distal end 66a along the direction of elongation. The cannulated body 62a is substantially straight and is connected to a handle 67a at the proximal end 64a. The opening assembly 52 further includes a flexible or elastic elongate opening device 62b, which is sized to be received in the cannula 68a. The opening device 62b can include a proximal end 64b and an opposed distal end 66b, and a cannula 68b that extends through the opening device 62b from the proximal end 64b to the distal end 66b. The opening device 62b is connected to a handle 67b at the proximal end 64b. The cannulas 68a-b can extend through the respective handles 67a-b. The distal end 66b can provide a cutting blade 65 or alternatively configured opening member that is configured to cut through the target bone. The opening device 62b is curved at a location proximate to the distal end 66b, and is further flexible, such that the distal end 66b is disposed in the cannula 68a in a straight configuration, but is bent when disposed outside of the cannula 68a. The opening device 62b can be formed from any suitable elastic bent material, such as Nitinol (or a nickel-titanium alloy). The opening device 62b can thus be shaped so as to correspond with the size and shape of the target bone, such as a target vertebra 70. The system 50 can include a pair of symmetrically shaped opening assemblies 52 that can be inserted into the target vertebra 70.

Figure 5A:
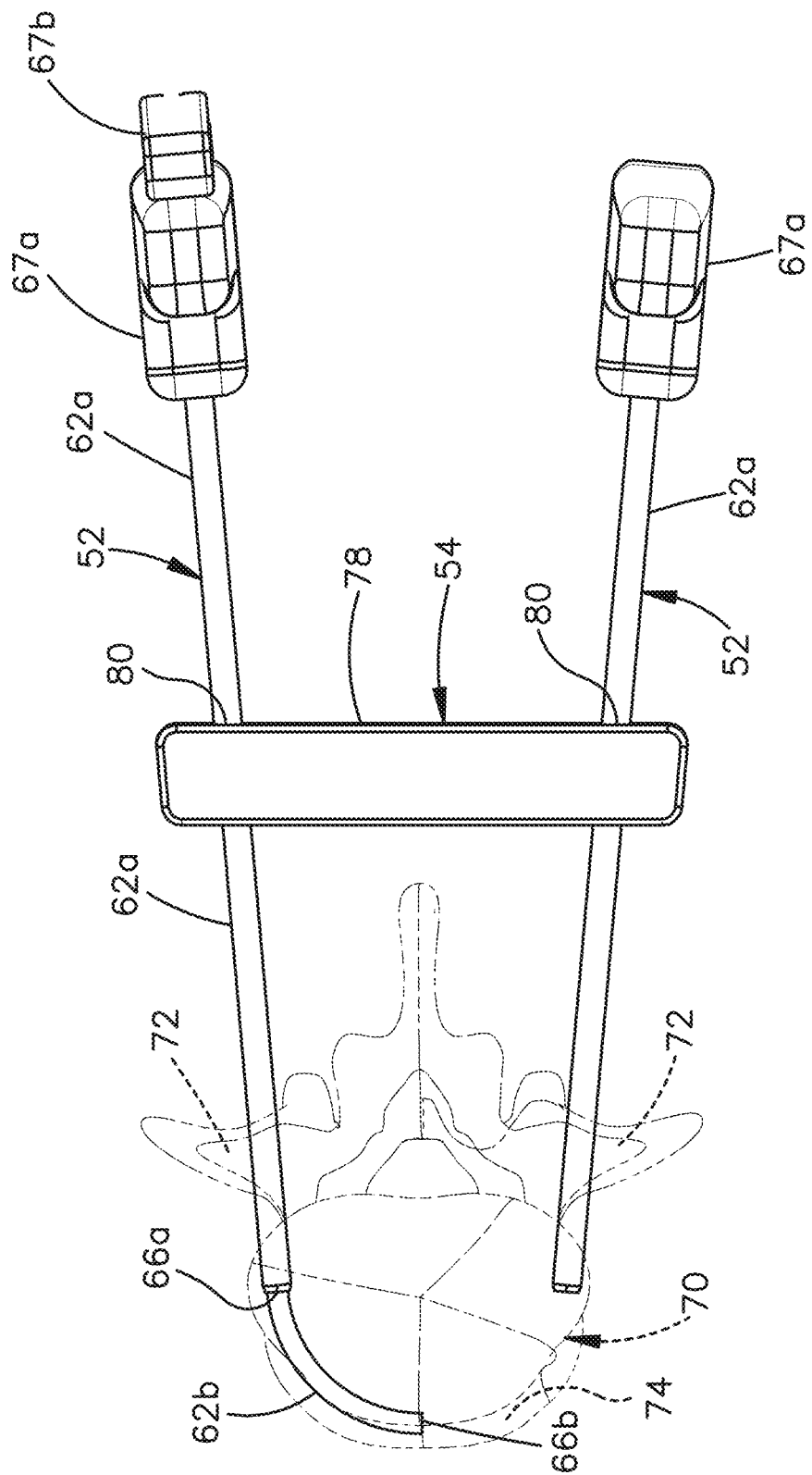
FIG. 5A is a schematic top plan view of a pair of opening assemblies inserted into a vertebra, wherein each opening assembly includes a cannula and an opening device received in the cannula.

During operation, the opening devices 62b can be inserted into the proximal end 64a of the cannulated body 62a, such that the curved portion of the opening device 62b extends out from the distal end 66a of the cannulated body 62a. For the purposes of illustration, FIG. 5A shows one of the cannulated bodies 62a receiving a cutting device 62b, while the other cannulated body 62a does not retain a cutting device. FIG. 6B shows a pair of opening assemblies 52, each having a cannulated body 62 and a cutting device 62b disposed in the cannula of each cannulated body 62. In accordance with one embodiment, the opening devices 62b can be inserted into the vertebra 70 along a transpedicular approach. A stab incision can be used to access the pedicles 72 of the target vertebra 70, under intra-operative radiological observation. Both pedicles 72 of the targeted vertebral body 74 can be opened by driving the distal cutting ends 65 into the respective pedicles 72, such that the opening devices 62b penetrate the cortical bone of the corresponding pedicles 72. The opening devices 62b can then be translated along the pedicle axes, so as to perforate the arched channel through the cancellous bone within the vertebral body 74, as illustrated in FIG. 5A. The bent shape of the opening devices 62b causes the respective distal ends 66b to align and abut as desired.

Figure 5B:
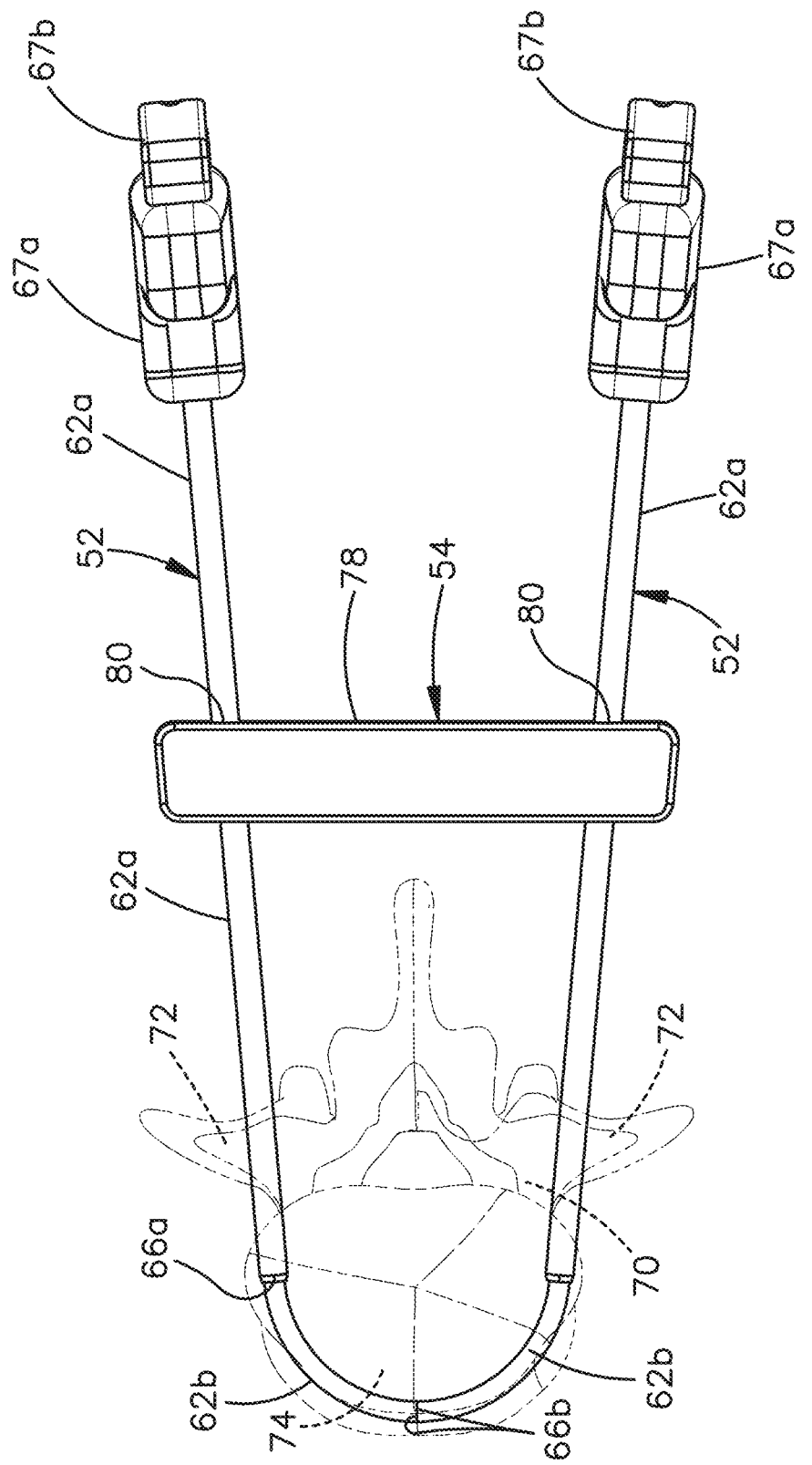
FIG. 5B is a schematic view of the opening assembly illustrated in FIG. 5A shown the opening devices in an aligned and abutting position.

The system 50 can further include an aiming device 54 that includes a body 78 and a pair of spaced apertures 80 extending through the body 78 sized to receive the corresponding pair of cannulated bodies 62a. The apertures 80 are aligned and spaced apart so as to be configured to allow the distal ends 66b of the corresponding opening devices 62b to be in operative communication with each other so as to facilitate insertion of the expandable implant 20. In accordance with the illustrated embodiment, the distal ends 66b are aligned and abut each other when inserted into the vertebral body 74, as shown in FIG. 5B.

Figure 6A:
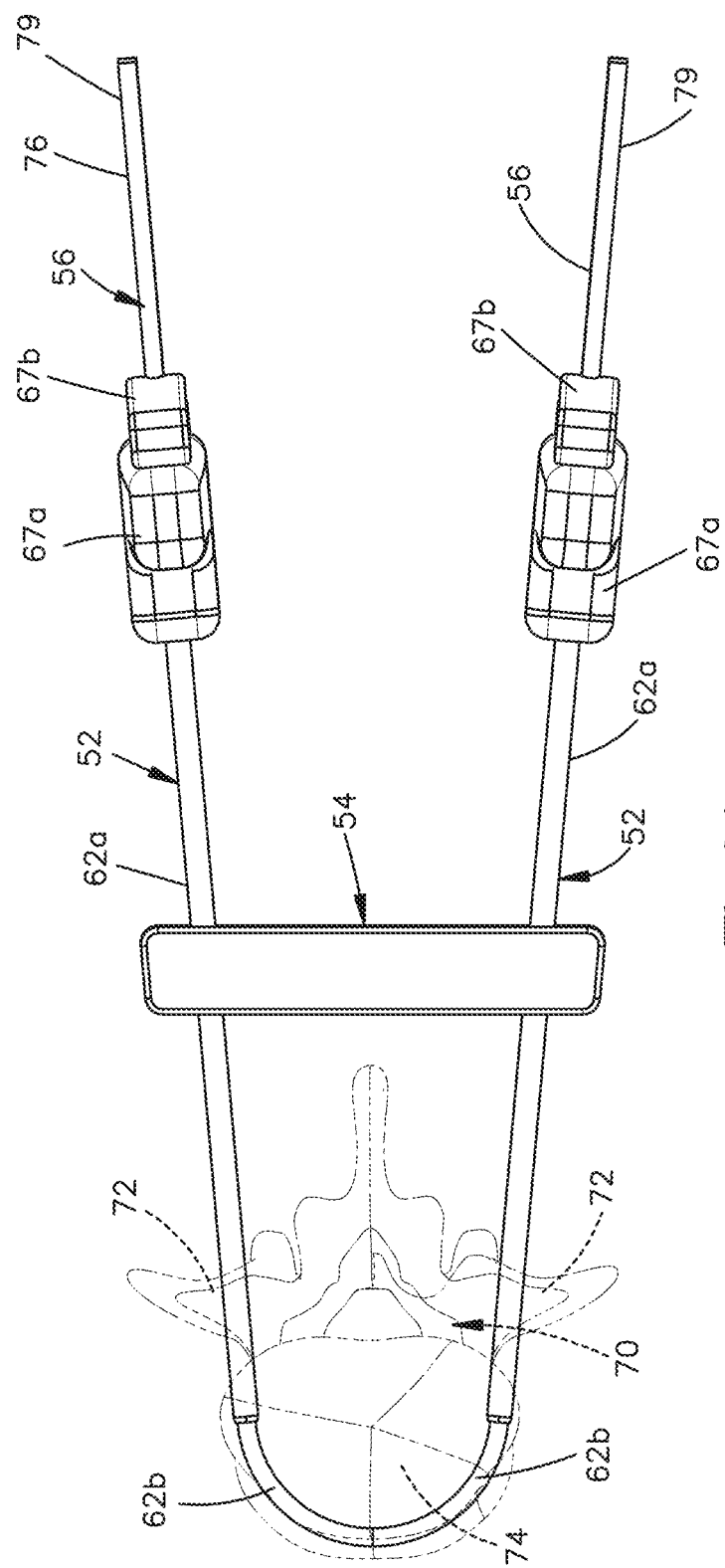
FIG. 6A is a perspective view of a cutting device inserted into the opening assemblies and into a target vertebral body.

Referring also to FIG. 6A, once the opening devices 52 are in place, the osteotomy cutting device 56 can be inserted through the cannula 68b of one of the opening devices 62b at the proximal end 64b, through the distal end 66b of the opening device 62b, into the distal end 66b of the adjacent opening device 62b, and through the proximal end 64b of the adjacent opening device 62b. As illustrated in FIGS. 6B-C, the cutting device 56 defines a body 76 having a pair of opposed ends 79, and a cutting portion 81 disposed centrally between the opposed ends 79. The ends 79 can each be threadeedly connected to the cutting portion 81 at respective joints 77. The body 76 can be sized to fit within the opening device 62b, which in turn is disposed in the cannulated body 62a. The cutting device body 76 can be made from a flexible wire material, so as to permit the cutting device 56 to travel through the curved cannulas 68. The body 76 can be longer than the pair of opening assemblies 52, such that the opposed ends 79 extend out of the proximal ends 64 of the opening assemblies 52 when the body 76 is disposed in the cannulas 68.

The cutting portion 81 can include a plurality of cutting members in the form of teeth 82 that retractably project out from the body 76. The cutting device 56 can further include a protective sleeve 84 that fits over the teeth 82. The sleeve 84 includes a sleeve body 85 and a plurality of apertures 86 extend through the sleeve body 85. The apertures 86 are sized to receive the respective teeth 82. The sleeve 84 can be disposed at a first guard position (FIG. 6B) relative to the teeth 82, such that the body 85 is aligned with the teeth 82, and thus guard the teeth 82 from cutting adjacent structure. The sleeve 84 can be moved to a second cutting position (FIG. 6C) relative to the teeth 82 such that the apertures 86 are aligned with the teeth 82. The teeth 82 can be biased to extend out from the cutting body 76 and through the apertures 86 when the apertures 86 are aligned with the teeth 82, such that the teeth 82 are configured to cut adjacent structure.

During operation, the cutting body 76 is inserted through one of the opening devices 62b with one end 79 attached to the cutting portion via the joint 77. The cutting portion is inserted into the respective proximal end 64b, through the distal end 66b, into the distal end 66b of the adjacent opening device 62b. The opposing end 79 is then inserted into the proximal end 64b of the adjacent opening device 62b and is inserted into the opening device 62b until it contacts the joint 77, at which point the opposing end 79 is rotated so as to threadedly connect the end 79 to the cutting portion 81. Accordingly, the opposed ends 79 of the cutting device 56 extend out from the proximal ends 64a of the opening devices 62b.

Once the cutting device 56 is in place, the opening devices 62b can be removed while the cutting device 56 remains in place as shown in FIG. 6D. The sleeve 84 can then be moved to the cutting position. For instance, the sleeve 84 can extend to one or both of the opposed ends 79 such that it can be manually translated to the cutting position, or an actuator can extend out of the proximal end 64b of one or both of the opening devices 62b, and can be actuated so as to iterate the sleeve 84 to the cutting position. With the opening devices 62b removed, and the cutting teeth 82 extending through the apertures 86, the opposed ends 79 can be translated back and forth, thereby causing the cutting teeth 82 to cut through the cortical bone to perform the osteotomy. As illustrated in FIG. 6D, handles 83 can be attached to the opposed ends 79 of the cutting device body 76 to assist in the cutting motion. Once the cortical bone is cut through, the sleeve 84 can spring back to its guard position. For instance, the teeth 82 can have a beveled surface that rides along the sleeve body 85 and causes the teeth 82 to retract as the sleeve body 85 translates to the guard position.

Figure 6E:
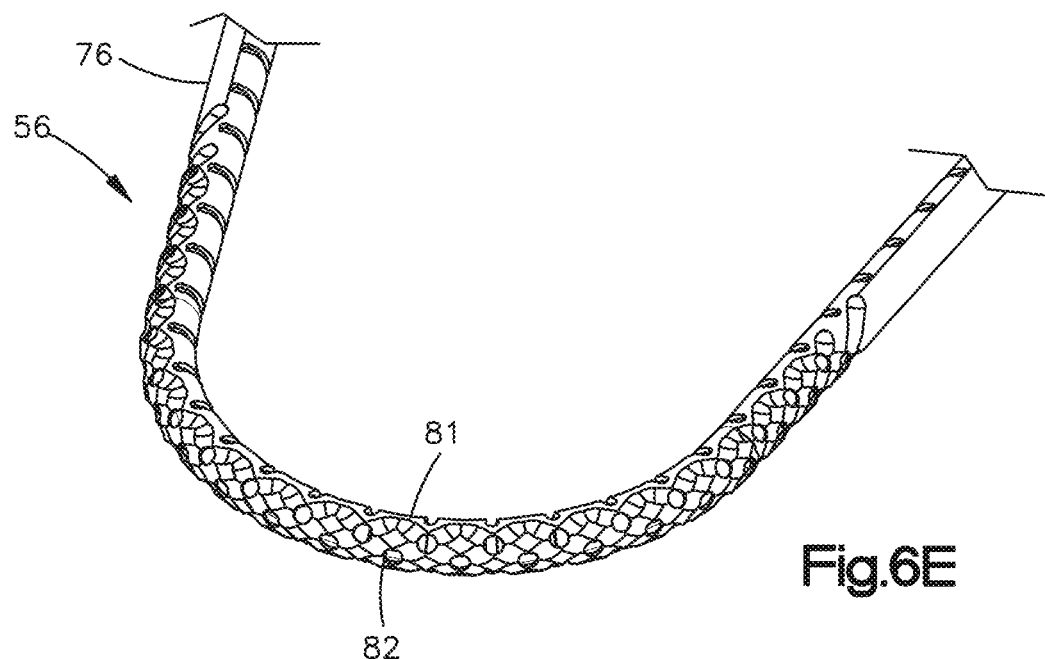
FIG. 6E is a perspective view of a portion of a cutting device constructed in accordance with an alternative embodiment.
Figure 6F:
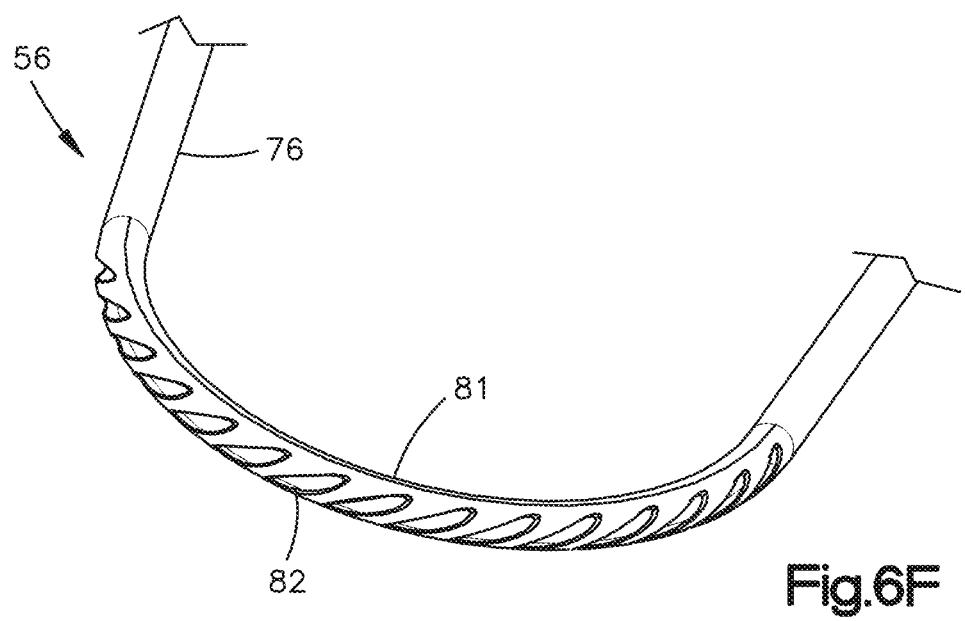
FIG. 6F is a perspective view of a portion of a cutting device constructed in accordance with another alternative embodiment.

Referring now to FIG. 6E, the cutting device 56 can be constructed in accordance with an alternative embodiment so as to not include the sleeve 84. The cutting members 82 are illustrated as diamond-shaped teeth that are configured to shave the cortical bone as the cutting device 56 is iterated back and forth. As illustrated in FIG. 6F, the cutting members 82 can be provided as apertures that extend through the cutting body at an orientation that defines a negative chip angle.

Figure 7A:
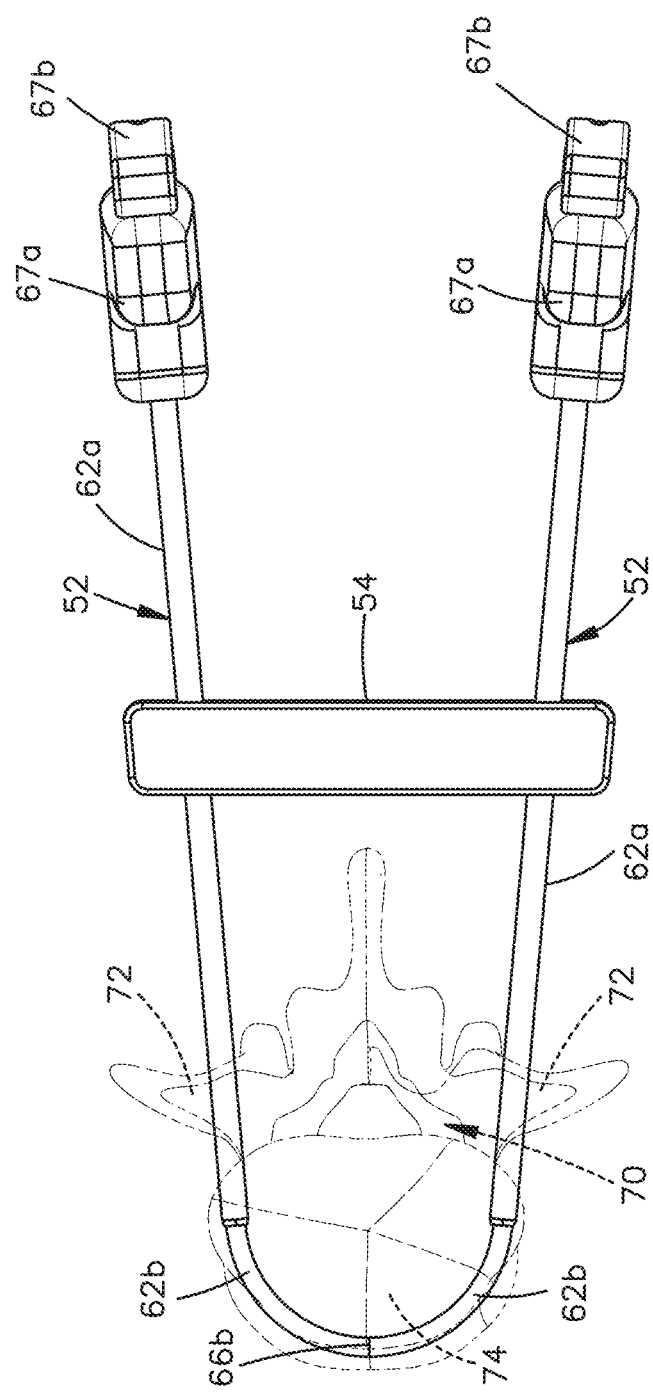
FIG. 7A is a schematic view of the opening devices inserted into the vertebra after an osteotomy has been performed.
Figure 7B:
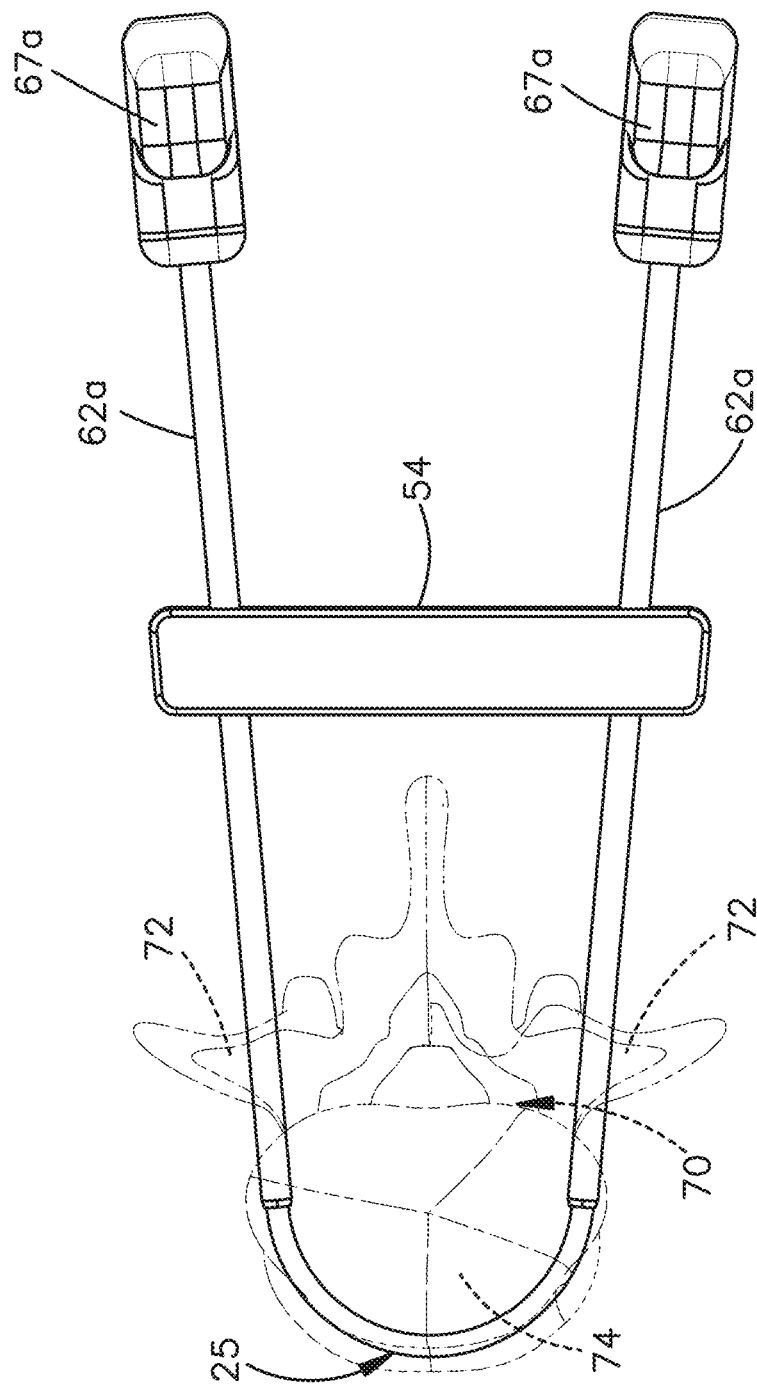
FIG. 7B is a schematic view of an installed implant assembly installed in the target vertebra in its insertion configuration.

Referring now to FIG. 7A, after the osteotomy has been completed, the opening devices 62b are again inserted into the cannulated bodies 62a and into the target vertebra 70 in the manner described above, such that the distal ends 66b are disposed proximate to the fracture location and abut each other. As illustrated in FIG. 7B, once the opening devices 52 have been inserted into the vertebra 70, the expandable implant assembly 25 is inserted into the opening device 62 and subsequently expanded, as will now be described.

In particular, referring now to FIGS. 4A-D and FIGS. 7A-C, the expansion device 58 can include an expansion body 96 that can be made from rubber, plastic, or other suitable material that provides an expandable bladder or other flexible member configured to occupy the internal void 23 of the implant body 22. The expansion device 58 defines a bore 97 that extends through the expansion body 96, sized to receive the guide wire 60. The body 96 is closed at a distal end 105, and open at a proximal end 107. As illustrated in FIG. 4D, the expansion implant 20 is placed over the expansion device 58 so as to provide an expandable implant assembly 25. The outer diameter of the expansion assembly 25, defined by the outer diameter of the expandable implant 20, is sized to fit within the opening device 62b, such that the expansion assembly 25 can be driven through the opening device 62b. The bore 97 receives the guide wire 60, such that the guide wire 60 can be driven into the opening device 62b, thereby causing the implant assembly 25 to ride into the target vertebral body 74. In this regard, it should be appreciated that the cannulated body 62a, the opening device 62b, and the guide wire 60, both alone and in combination, at least partially define or define a guide path for the expandable implant assembly 25, including the implant 20 and the expansion device 58.

Figure 7D:
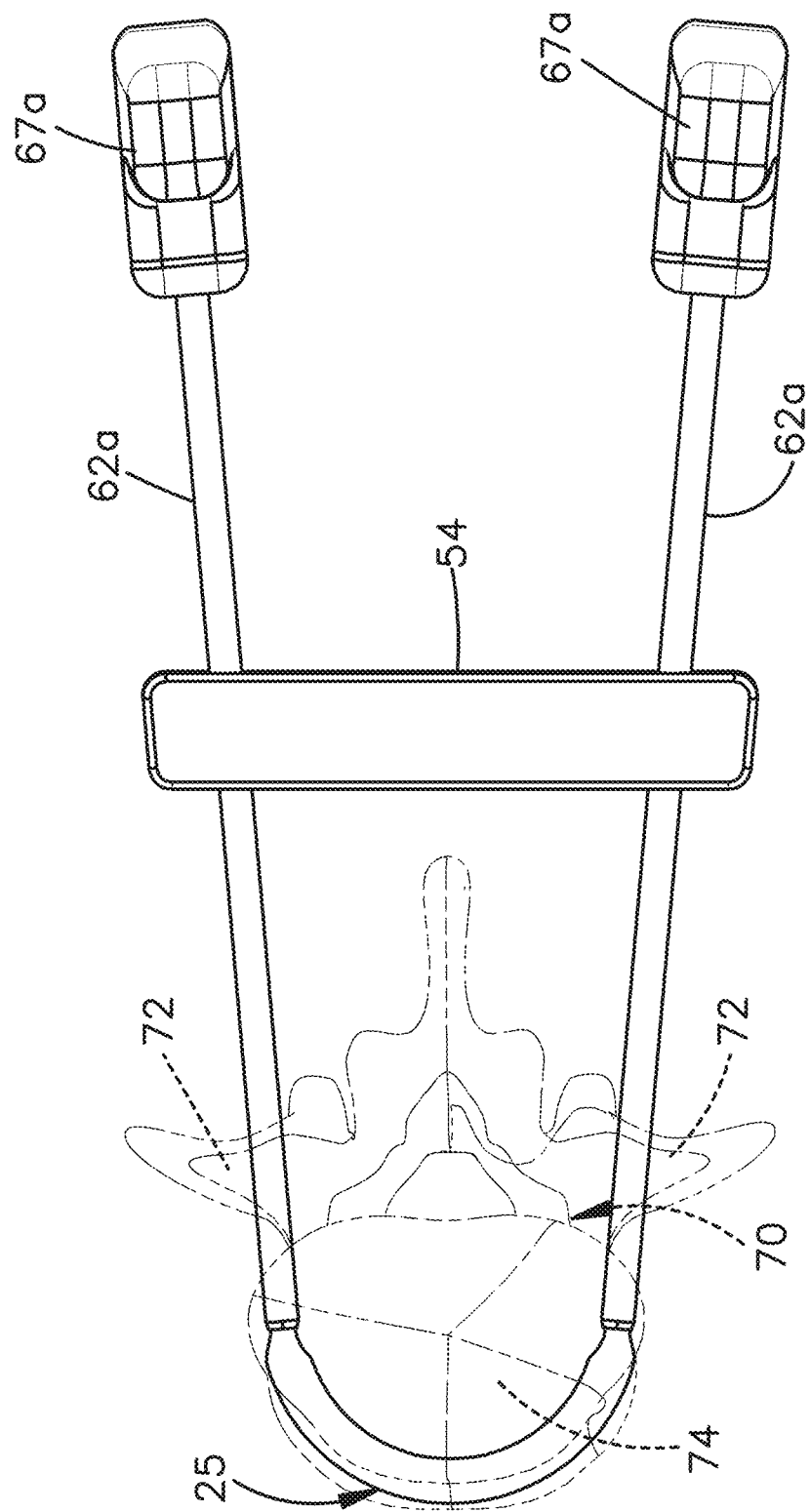
FIG. 7D is a schematic view of the installed implant assembly illustrated in FIG. 7B, but in the expanded configuration.

As illustrated in FIG. 7A, the opening devices 62b are driven through the cannulated bodies 62a such that their distal ends 66b abut each other in the manner described above. Next, as illustrated in FIG. 7B, the expansion assembly 25 is driven through the opening devices 62b into the vertebral body such that it is disposed between the bone fragment created during the osteotomy and the remaining integral bone portion, and the opening devices 62b are subsequently removed. The expansion device body 96 can have a sufficient length such that the proximal end 107 extends into the opening device 62b, and optionally extends out of the proximal end 64b when the implant 20 is disposed at the target vertebral body 74. The expansion device body 96 can be divided into a plurality of body segments 98 that are hingedly connected to each other at respective joints 103 so as to move with respect to each other about the joint. Accordingly, the expansion device body 96 can flex between adjacent segments 98 as it travels into the vertebral body 74 as illustrated in FIG. 7C. The implant 20 can thus be provided as at least one link 102, such as a plurality of separate discrete links 102 spaced apart along the column direction. Each link 102 can define at least one column of linkages 26 and at least one row of linkages 26 as described above. The links 102 can be mounted onto the respective body segments 98 in a substantially flat insertion configuration until the expansion assembly 25 is disposed in the vertebral body, at which point the filler material 59, such as cement or similar solid filler device, is injected into the bore 97 through the proximal end 107 of the expansion device 58 under a positive pressure, for instance using a piston pump or a syringe, as illustrated in FIGS. 7C-D. The positive pressure created by the filler material 59 causes the body 96 to expand against the respective link 102, which causes the links 102 to expand in the manner described above.

The expandable implant 20 can thus be expanded from the insertion configuration to the expanded configuration via injection of the bone filler material into the inner cavity of the expandable implant using any suitable injection device. Expansion of the expandable implant 20 compresses the surrounding cancellous bone tissue in the interior volume of the targeted bone thereby forming a cavity. Expansion of the expandable implant also preferably repositions and stabilizes the surrounding bone and/or bone tissue, thereby restoring the anatomical alignment of the fracture bone until hardening of the injected bone filler material.

Because the filler material is injected into the bore 97 of the expansion body, and the bore 97 is disposed in the internal void 23 of the expansion implant 20, it can thus also be said that the filler material is injected into the void 23 of the expansion implant 20. Thus, the implant 20 can expand substantially uniformly, for instance when all of the linkages 26 are substantially identically constructed, or can bend as it expands, for instance when a first plurality of the linkages 26 has an expansion characteristic, such as a size, different than a second plurality of the linkages 26 (for instance a greater length that provides greater expansion). The implant 20 is fixed in the expanded configuration when the bone filler, such as cement, hardens and/or cures.

The expansion device 58 includes a weakened neck 109 disposed between the proximal end 107 and the links 102. For instance, the neck 109 can have material removed and is thus configured to break away from the remaining portion of the expansion device body 96. Once the bone filler material 59 has hardened and/or cured, a rotational force can be applied to the proximal end 107 of the expansion device body 96, causing the body 96 to break at the neck 109, such that the section of the body 96 that is disposed proximal to the links 102 can be removed along with the bone filler material disposed in the bore 97 of the removed section. Alternatively, the body 96 can be closed immediately proximate to the links 102 such that the entire body 96 is inserted into the vertebral body 74, and a syringe can pierce the body 96 so as to inject the bone filler material into the bore 97.

Thus, during use, the cortical aspect of the targeted bone is opened using, for example, an awl or other cortex opening instrument. Once an osteotomy is performed, the expandable implant 20 can then be inserted in a straight configuration. Expansion of the implant 20 enables the joint surface or other aspects of the bone to be repositioned or even distracted. Expansion of the implant 20 causes the implant to become bent due to its specific design properties. As such, the implant 20 allows a more sophisticated repositioning of the fragment. It should be further appreciated that the expandable implant 20 can be inserted into a target bone via a minimally invasive apparatus or system.

Figure 7E:
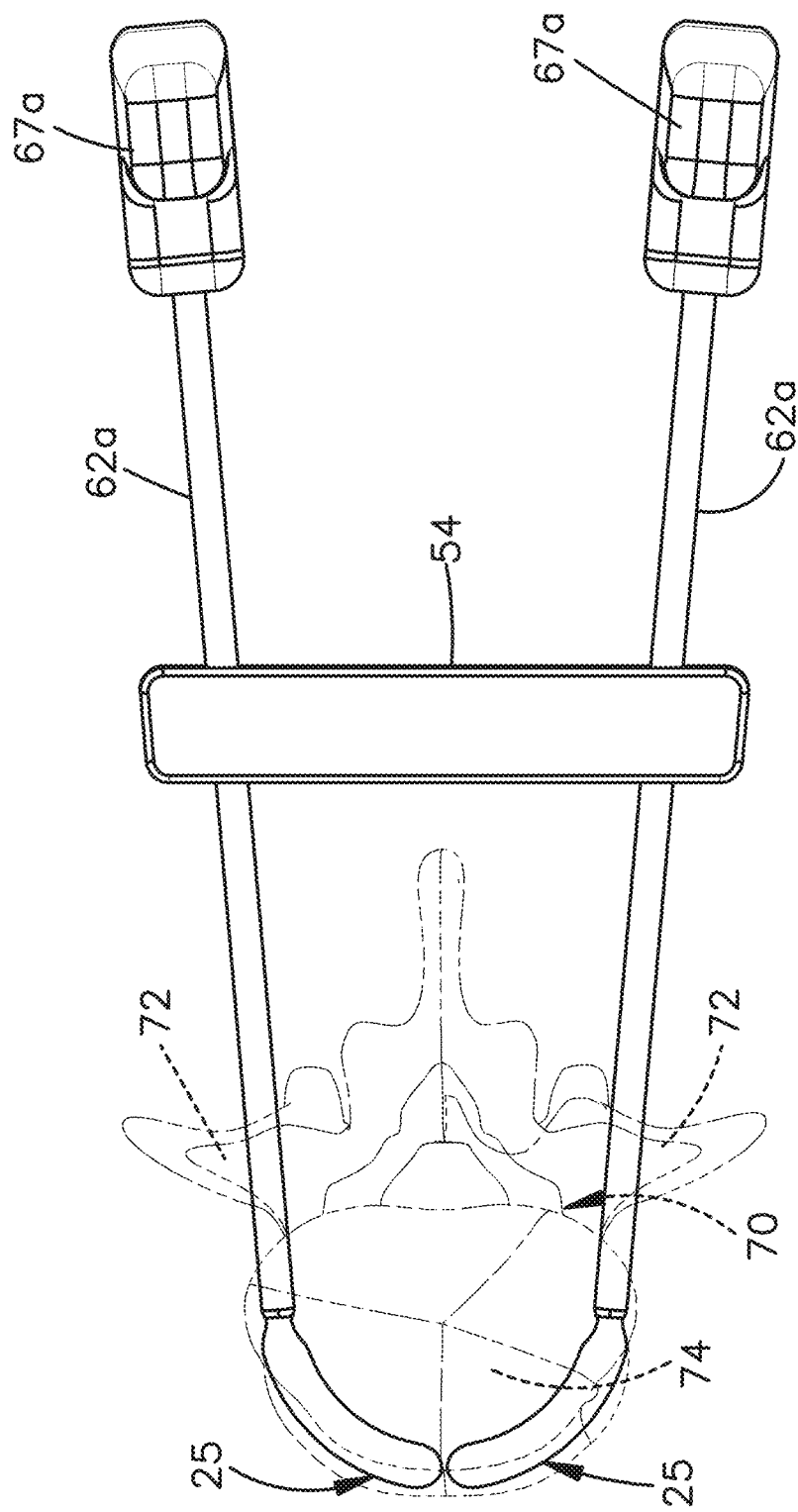
FIG. 7E is a schematic view of a pair of installed implant systems installed in the target vertebra in the expanded configuration.

In accordance with an alternative embodiment, FIG. 7E illustrates that the implant system 50 can include a pair of implant assemblies 25, each constructed as described above, but having a shortened length such that they extend substantially midway into the target vertebral body 74. Accordingly, one implant assembly 25 can be disposed at a first side of the vertebral body 75, and the other implant assembly 25 is disposed at an opposed second side of the vertebral body 75. In accordance with one embodiment, the first and second sides comprise a medial side and a lateral side. Each implant assembly 25 can then be expanded independently of the other via the injection of the bone filler material 59 in the manner described above. Accordingly, the height of each implant 20 can be adjusted independently, thereby adjusting first and portions of the target vertebral body 74 independently with respect to each other.

Figure 8A:
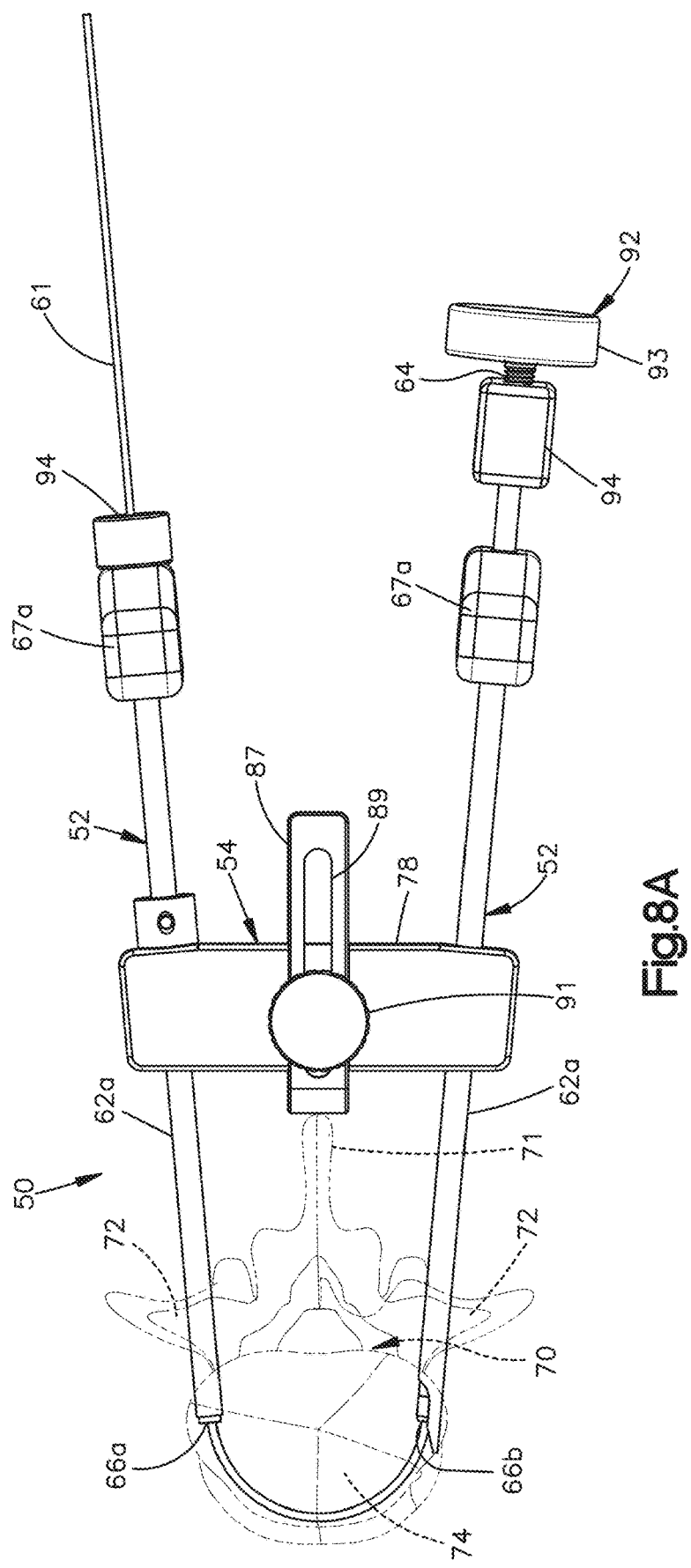
FIG. 8A is a schematic view of an opening device and a clamp, showing a guide wire inserted through the opening device and engaged at one end by the clamp.
Figure 8B:
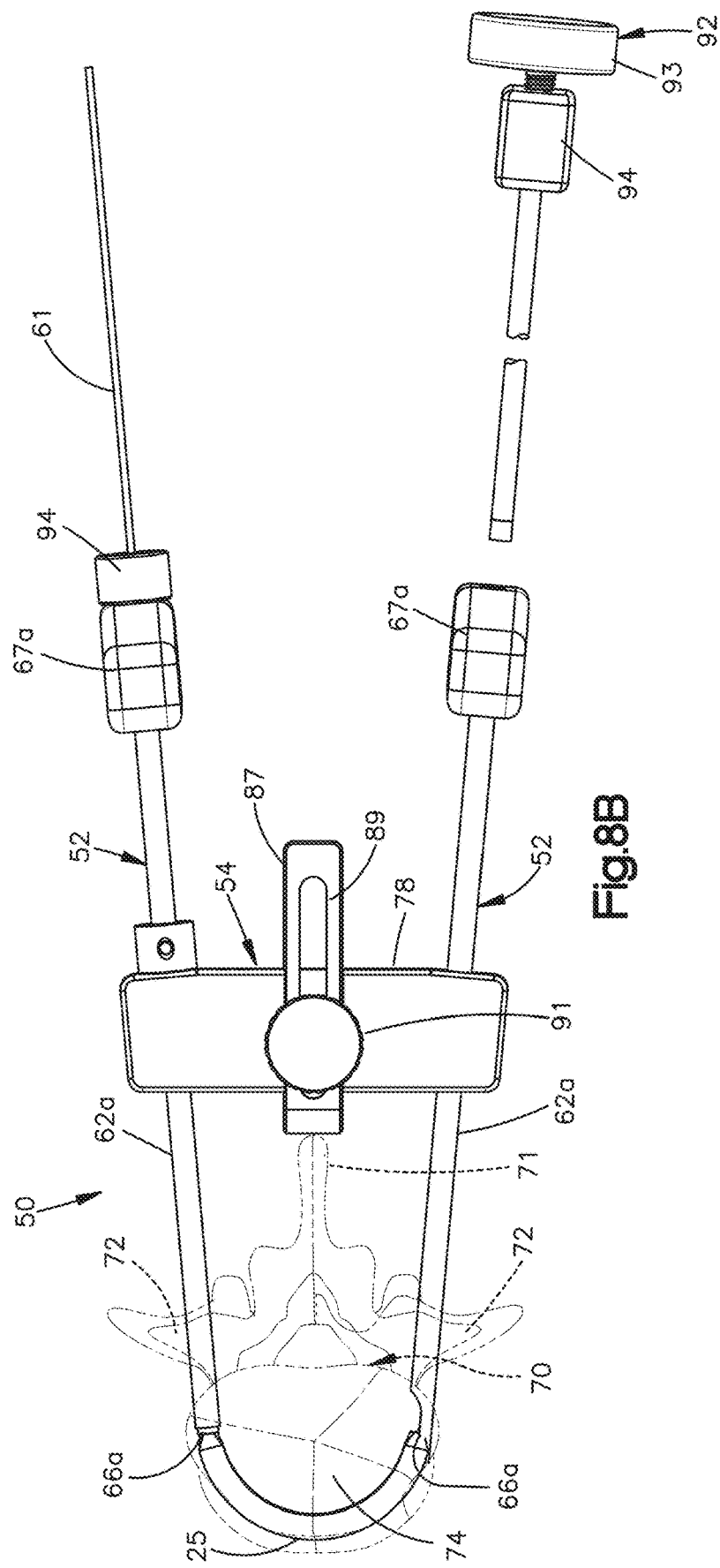
FIG. 8B is a schematic view similar to FIG. 8A, but showing an expandable implant assembly installed over the guide wire.

Referring now to FIGS. 8A-B, the system 50 can be constructed in accordance with an alternative embodiment, whereby an osteotomy is performed, and the implant 20 is installed and expanded in the intervertebral body 74. In particular, the aiming device 54 can include an arm 87 that is coupled to the aiming device body 78 via a knob 91 that extends through an elongate slot 89 extending through the arm 87, and is further threadedly connected to the aiming device body 78. Accordingly, the arm 87 can be movable with respect to the aiming device body 78 when the knob 91 is loose, and fixed with respect to the body 78 when the knob is tightened. The arm 87 can abut the target vertebra 70, for instance at the spinous process 71, so as to provide a holder for the opening devices 52, and a positioner that locates the cannulated bodies 62a at a desired location and orientation, for instance aligned with the pedicles 72.

The opening assembly 52 include the straight cannulated body 62a and an opening device is provided as a wire 61 that is driven through the pedicles 72 in the manner described above with respect to the opening device 62b in FIGS. 7A-E. The wire 61 primarily differs from the opening device 62b in that the wire 61 is not cannulated. Once the wire 61 has been driven through the target vertebral body 74, the distal end of 66b of the wire 61 can be engaged by a clamp 92 that extends through the adjacent cannulated body 62a. The implant system 50 further includes a pair of handles 94 that are connected to the guide wire 61 at a location proximal of the handles 67a.

The opening wire 61 is thus inserted through one of the cannulated bodies 62a, and pushed through the cancellous bone of the vertebral body 74. The clamp 92 is inserted through the cannula 68 of the other opening device 52, and a knob 93 that is coupled to the clamp 92 can be actuated so as to bring the clamp 92 into engagement with the wire 61 such that the clamp 92 retains the wire therein. The knob 93 can then be pulled, thereby drawing the wire 61 through the adjacent cannulated body 62b until the terminal end of the wire 61 extends through the proximal end of the cannulated body 62b or handle 67a. It should be appreciated that the wire 61 can be bent such that as it is driven through the cannulated body 62a, it extends around the vertebral body 74 to the clamp 92. In this regard, the wire can be made from any suitable bent and elastic material, such as Nitinol (or a nickel-titanium alloy). The guide wire 61 can presents one or more cutting teeth at a cutting portion 111 that is disposed at the vertebral body 74 once the guide wire 61 has been pulled through by the clamp 92.

Accordingly, by iterating the wire 61 back and forth against the vertebral body 74, the wire can cut through the cortical bone so as to perform an osteotomy. The wire 61 can then be removed. Alternatively, one end 79 of a cutting device 56 of the type described above can be attached to one end of the wire 61, and the wire 61 can be pulled through the cannulated bodies 62a so as to guide the cutting device 56 into the cannulated bodies 62a such that the cutting portion 81 is disposed at the vertebral body 74 in the manner described above.

Once the osteotomy has been completed, the augmentation implant 20 can be inserted between the bone fragment created during the osteotomy and the remaining integral portion of the vertebral body 74, and subsequently expanded in the manner described above with respect to FIGS. 7A-E.

Certain example embodiments have been described with respect to an expandable implant (e.g., a stent), which in combination with injected bone filling material (e.g., bone cement) may be used to augment an interior volume of a target bone, restoring the height of the bone, filling a cavity formed in the bone and/or for stabilizing, aiding and/or augmenting the bone. It should be appreciated that while the expandable implant 20 has been described as used in a target bone that has been illustrated as the spine (for example, in the lumbar, thoracic or cervical regions), those skilled in the art will appreciate that the implant 20 may be used in other parts of the body, for instance to augment an alternative target bone, including for example long bones such as proximal humerus and proximal tibia or bones in the hand, face, feet, extremities, cranium, or in nearly any bone in the human body.

Figure 9A:
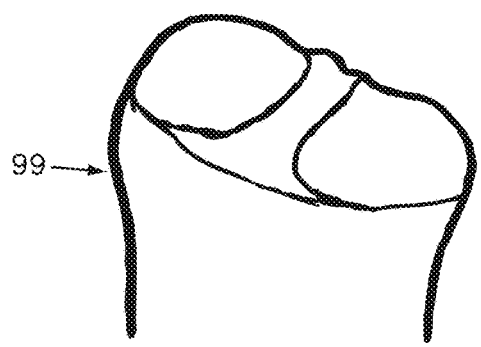
FIG. 9A is a perspective view of a normal tibia plateau.
Figure 9C:
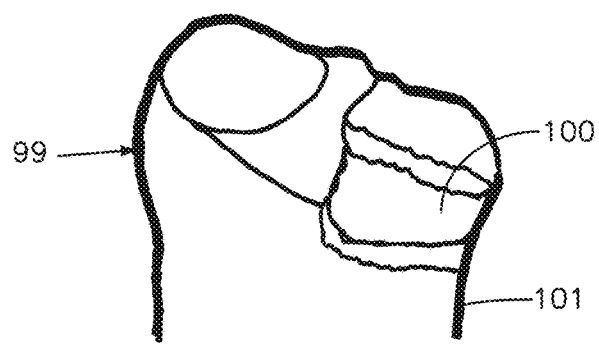
FIG. 9C is a perspective view similar to FIG. 9A, but showing the tibia plateau fractured.
Figure 9B:
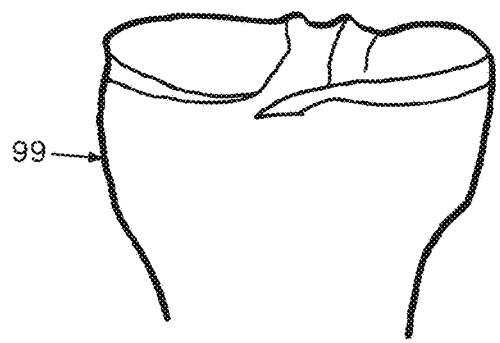
FIG. 9B is an anterior view of the normal tibia plateau illustrated in FIG. 9A.
Figure 9D:
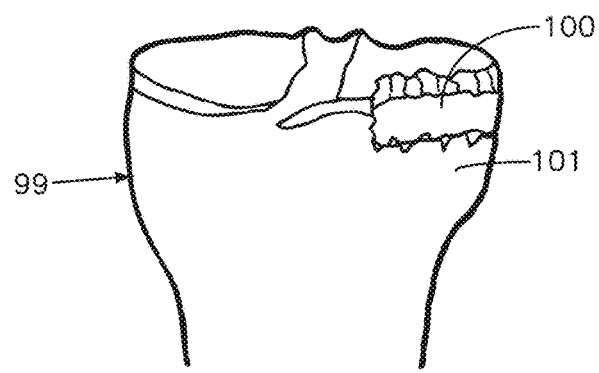
FIG. 9D is an anterior view of the fractured tibia plateau illustrated in FIG. 9E.
Figure 9E:
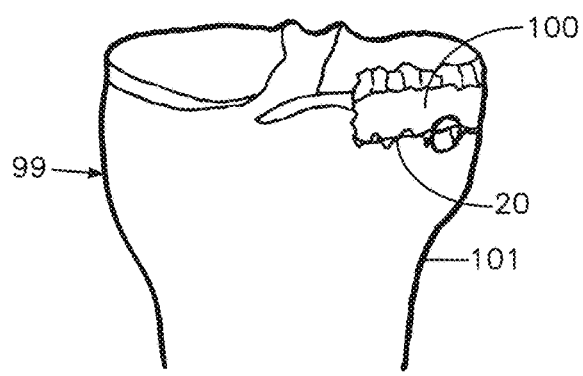
FIG. 9E is an anterior view of the fractured tibia plateau illustrated in FIG. 9D, but showing an expandable implant assembly implanted in an insertion configuration at the fracture site.
Figure 9F:
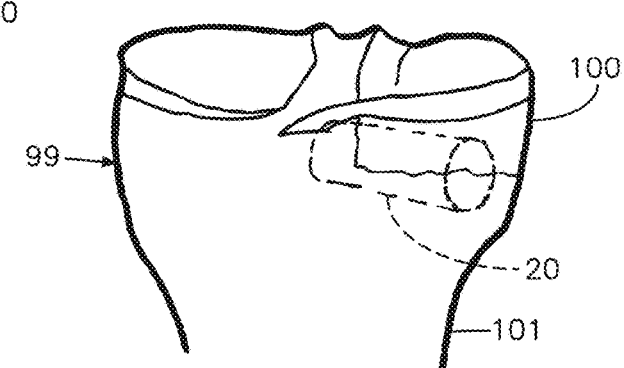
FIG. 9F is an anterior view of the fractured tibia plateau illustrated in FIG. 9E, but with the implant assembly in an expanded configuration so as to restore the normal height to the tibia plateau.

For instance, referring now to FIGS. 9A-E, the target bone is a tibia plateau 99, illustrated in its natural state in FIGS. 9A-B. FIGS. 9C-D illustrated the tibia plateau 99 as fractured so as to produce a tibia fracture fragment 100 that is separate from a remaining integral bone portion 101 of the tibia plateau 99. Referring to FIG. 9E, after the fracture fragment 100 has been mobilized and repositioned, the implant assembly 25 is inserted in a straight configuration between the integral bone portion 101 and the fracture fragment 100. In this regard, it should be appreciated that a bone fracture fragment can be produced during an osteotomy, or due to a fracture caused, for instance, from injury. The bone filler material is then inserted into the bore 97 that extends through the expansion body 96 in the manner described above. As the implant 20 expands and bends, the fracture fragment is repositioned as illustrated in FIG. 9F. The implant 20 is fixed in the expanded configuration when the bone filler, such as cement, hardens and/or cures so as to restore the height of the fractured tibia plateau to its normal height It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention as defined by the present description.

The invention claimed is:

1. An implant insertion assembly, comprising:
a first cannulated body having a distal end that is configured to be positioned adjacent a target bone, wherein the first cannulated body is substantially straight from the distal end to a proximal end spaced from the distal end;
an opening device that is elongate and configured to advance through the first cannulated body, the opening device defining a distal end that is configured to advance distally beyond the distal end of the first cannulated body and cut into the target bone, wherein at least a portion of the opening device located proximally from the distal end is configured to extend 1) substantially axially straight while located within the first cannulated body and 2) axially curved after extending beyond the distal end of the first cannulated body such that the distal end of the opening device cuts a curved guide path within the target bone;
a second cannulated body having a proximal end and a distal end that are spaced from each other, wherein the distal end of the second cannulated body is configured to be positioned adjacent the target bone at a location spaced from the distal end of the first cannulated body, wherein the second cannulated body is substantially straight from its proximal end to its distal end;
an aiming device having a body that defines a pair of apertures spaced from one another and each extending through the body, wherein the pair of apertures are configured to receive the first and second cannulated bodies, respectively, so that the distal end of the first cannulated body and the distal end of the second cannulated body are each positioned adjacent the target bone at a desired spacing relative to one another; and
an implant insertable within at least the first cannulated body and along the opening device and along the curved guide path within the target bone, the implant defining a central axis that is curved while the implant is positioned along the curved guide path, and the implant is expandable outwardly along a direction perpendicular to the central axis.

2. The implant insertion assembly of claim 1, wherein the at least the portion of the opening device is formed of an elastic material that is pre-bent according to a geometry of the target bone.

3. The implant insertion assembly of claim 2, wherein the elastic material is nitinol.

4. The implant insertion assembly of claim 1, further comprising a second opening device that is elongate and configured to advance through the second cannulated body, the second opening device defining a distal end that is configured to advance distally beyond the distal end of the second cannulated body and cut into the target bone, wherein at least a portion of the second opening device located proximally from the distal end thereof is configured to extend 1) substantially axially straight while located within the second cannulated body and 2) axially curved after extending beyond the distal end of the second cannulated body such that the distal end of the second opening device cuts a second curved guide path and abuts the distal end of the first opening device within the target bone.

5. The implant insertion assembly of claim 4, wherein the first and second opening devices each defines a cannula configured to allow advancement of the implant therethrough and into the target bone.

6. The implant insertion assembly of claim 5, further comprising a cutting device insertable through the cannulas of the first and second opening devices and through the at least the portions of the first and second opening devices, wherein the first and second opening devices are each configured to be at least partially withdrawn from the first and second cannulated bodies, respectively, so as to expose cutting features of the cutting device to the target bone along the curved guide paths.

7. The implant insertion assembly of claim 6, wherein the cutting device further comprises:
  a body having opposed ends;
  a cutting portion that includes the cutting features, wherein the cutting portion is disposed between the opposed ends, the opposed ends are sized so as to extend proximally from the proximal ends of the first and second cannulated bodies, respectively, and the opposed ends are configured to be gripped so as to translate the cutting portion back and forth along the curved guide paths, thereby performing an osteotomy in the target bone.

8. The implant insertion assembly of claim 7, wherein the cutting device further comprises a protective sleeve configured to iterate between a first position in which the protective sleeve covers the cutting features and a second position in which the cutting features are exposed to the target bone.

9. The implant insertion assembly of claim 8, wherein the cutting features are teeth, and the protective sleeve includes a plurality of apertures configured to be 1) offset from the teeth when the protective sleeve is in the first position, and 2) aligned with the teeth when the protective sleeve is in the second position.

10. The implant insertion assembly of claim 9, wherein the teeth are biased so as to extend outwardly from the cutting portion and through the plurality of apertures so as to cut adjacent structure of the target bone when the protective sleeve is in the second position.

11. The implant insertion assembly of claim 5, wherein the implant is insertable through the first cannulated body and through the cannula of the first opening device and into the cannula of the second opening device so as to reside along the curved guide paths within the target bone, and the central axis is curved while the implant is positioned along the curved guide path before and after expansion.

12. The implant insertion assembly of claim 11, wherein the implant comprises an implant body elongate along the central axis, the implant body having a plurality of linkages connected so as to define at least one annular row of linkages arranged in a plurality of columns, each of the plurality of linkages defining a first side and a second side circumferentially spaced from the first side about the central axis, wherein the linkages are configured such that a distance between the first and second sides of each of the linkages increases as the implant expands.

13. The implant insertion assembly of claim 5, wherein:
  the implant is a first implant that is insertable through the first cannulated body and through the cannula of the first opening device along the curved guide path within the target bone; and
  the implant insertion assembly further comprises a second implant that is insertable through the second cannulated body and through the cannula of the second opening device along the second curved guide path within the target bone, wherein the second implant defines a second central axis, and the second implant is expandable outwardly along a respective direction perpendicular to the second central axis, and the second central axis is curved while the second implant is positioned along the second curved guide path before and after expansion of the second implant.

14. The implant insertion assembly of claim 13, wherein each of the first and second implants comprises an implant body elongate along the central axis, the implant body having a plurality of linkages connected so as to define at least one annular row of linkages arranged in a plurality of columns, each of the plurality of linkages defining a first side and a second side circumferentially spaced from the first side about the central axis, wherein the linkages are configured such that a distance between the first and second sides of each of the linkages increases as the implant expands.

15. The implant insertion assembly of claim 1, wherein the opening device is a guide wire insertable through one of the first and second cannulated bodies and beyond the distal end thereof, such that the distal end of the guide wire is configured to cut the curved guide path within the target bone to the distal end of the other of the first and second cannulated bodies, wherein the guide wire is further insertable through the other of the first and second cannulated bodies.

16. The implant insertion assembly of claim 15, further comprising a clamp insertable within the other of the first and second cannulated bodies, wherein the clamp is configured to engage and selectively retain the distal end of the guide wire and pull the guide wire such that portions of the guide wire extend proximally beyond the proximal ends of the first and second cannulated bodies.

17. The implant insertion assembly of claim 16, wherein the guide wire includes a cutting portion defining cutting teeth, wherein the cutting portion is configured to iterate back and forth within the curved guide path so as to perform an osteotomy on the target bone.

18. The implant insertion assembly of claim 15, wherein the implant defines a central bore configured to receive the guide wire, such that the implant is configured to ride along the guide wire and advance through one of the first and second cannulated bodies and into the curved guide path within the target bone.

19. The implant insertion assembly of claim 18, further comprising an expansion device received within the central bore of the implant so as to carry the implant, the expansion device defining a central bore configured to receive the guide wire, and the expansion device and the implant are configured to ride along the guide wire and advance through the one of the first and second cannulated bodies and into the curved guide path within the target bone, wherein the expansion device is configured to be filled with a material under pressure so as to expand the expansion device against the implant along the direction perpendicular to the central axis.

* * * * *